(12) United States Patent
Malaspina

(10) Patent No.: US 9,714,450 B2
(45) Date of Patent: Jul. 25, 2017

(54) METHODS FOR DIAGNOSING AND TREATING SCHIZOPHRENIA

(71) Applicant: Dolores Malaspina, New York, NY (US)

(72) Inventor: Dolores Malaspina, New York, NY (US)

(73) Assignee: New York University, New York, NY (US)

(*) Notice: Subject to any disclaimer, the term of this patent is extended or adjusted under 35 U.S.C. 154(b) by 259 days.

(21) Appl. No.: 14/016,597

(22) Filed: Sep. 3, 2013

(65) Prior Publication Data

US 2014/0066461 A1 Mar. 6, 2014

Related U.S. Application Data

(60) Provisional application No. 61/695,597, filed on Aug. 31, 2012.

(51) Int. Cl.
*C12Q 1/68* (2006.01)
*A61K 31/519* (2006.01)

(52) U.S. Cl.
CPC .......... *C12Q 1/6883* (2013.01); *A61K 31/519* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 7,982,036 B2 | 7/2011 | Singh et al. |
| 8,048,622 B2 | 11/2011 | Bly |
| 8,067,160 B2 | 11/2011 | Brennan et al. |
| 8,076,075 B2 | 12/2011 | Clelland et al. |
| 2011/0269688 A1 | 11/2011 | Hakonarson et al. |
| 2011/0311512 A1 | 12/2011 | Hakonarson et al. |

FOREIGN PATENT DOCUMENTS

WO 2013067264 5/2013

OTHER PUBLICATIONS rs7474275, dbSNP, NCBI, NLM.*
Malaspina et al., "Paternal age and sporadic schizophrenia: Evidence for de novo mutations", Am J Med Genetics (Neuropsychiatric Genetics), 2002, 114:299-303.
Carrera et al. "Association study of nonsynonymous single nucleotide polymorphisms in schizophrenia", Biol Psychiatry 2012; 71:169-177.
Xu et al., "Exonne sequencing supports a de novo mutational paradigm for schizophrenia", Nature Genetics, 2011, 43:864-869.
Ponader et al., "Activity of Bruton's tyrosine kinase (Btk) inhibitor pCI-32765 in Mantle Cell Lymphoma (MCL) identifies Btk as a novel therapeutic target", Blood (ASH Annual Meeting Abstracts) 2011 118: Abstract 3688.
Kozaki et al., "Development of a Bruton's Tyrosine Kinase (Btk) Inhibitor, ONO-WG-307: Efficacy in ABC-DLBCL Xenograft Model—Potential Treatment for B-Cell Malignancies", Blood, ASH Annual Meeting Abstracts, 2011 118: Abstract 3731.
Malaspina et al., "Advancing paternal age and the risk of schizophrenia.", Archives General Psychiatry. 2001; 58(4): 361-7.
Sipos et al., "Paternal age and schizophrenia: a population based cohort study", BMJ 2004; 329:1070.
Ei-Saadi et al., "Paternal and maternal age as risk factors for psychosis: findings from Denmark, Sweden and Australia.", Schizophr. Res. 2004; 67:227-236.
Zammit et al., "Paternal age and risk for schizophrenia", Br. J. Psychiatry 2003; 183:405-408.
Byrne et al., "Parental age and risk of schizophrenia: a case-control study", Arch. Gen. Psychiatry 2003; 60:673-678.
Dalman et al., "Paternal age and schizophrenia: further support for an association.", Am. J. Psychiatry 2002; 159:1591-1592.
Brown et al., "Paternal Age and Risk of Schizophrenia in Adult Offspring", Am. J. Psychiatry 2002; 159:1528-1533.
Tsuchiya et al., "Advanced paternal age associated with an elevated risk for schizophrenia in offspring in a Japanese population", Schizophr. Res., 2005; 76:337-342.
Malaspina et al., "Paternal age and intelligence: implications for age-related genomic changes in male germ cells", Psychiatr Genet. 2005; 15:117-25.
Hare et al., "Raised parental age in psychiatric patients: evidence for the constitutional hypothesis", Br J Psychiatry, 1979; 134:169-77.
Risch et al., "Spontaneous Mutation and Parental Age in Humans", Am. J. Hum. Genet., 1987; 41:218-248.
Olshan et al., "Paternal age and the risk of congenital heart defects", Teratology, 1994; 50:80-84.
Zhang et al., "Parental Age at Child's Birth and Son's Risk of Prostate Cancer, The Framingham Study", Am. J. Epidemiol., 1999; 150:1208-1212.
Fletcher et al., "Parental age, genetic mutation, and cerebral palsy", J. Med. Genet., 1993; 30:44-46.
Bertram et al., "Paternal age is a risk factor for Alzheimer disease in the absence of a major gene", Neurogenetics, 1998; 1:277-280.
Harlap et al., "Paternal age and preeclampsia", Epidemiology 2002; 13:660-667.
Montgomery et al., "Parental age, family size, and risk of multiple sclerosis", Epidemiology, 2004; 15:717-723.
Slama et al., "Influence of Paternal Age on the Risk of Spontaneous Abortion", Am. J. Epidemiol, 2005, 161:816-823.
Crow, "The origins, patterns and implications of human spontaneous mutation", Nature Reviews, 2000, 1:40-47.
Williams et al., "Support for genetic variation in neuregulin 1 and susceptibility to schizophrenia.", Mol. Psychiatry, 2003; 8:485-487.
Gulsuner et al., "Spatial and temporal mapping of de novo mutations in schizophrenia to a fetal prefrontal cortical network", Cell, 2013, 154:518-529.

(Continued)

*Primary Examiner* — Jehanne Sitton
(74) *Attorney, Agent, or Firm* — Klauber & Jackson LLC

(57) ABSTRACT

Genetic markers of schizophrenia (SCZ) are presented herein, as are methods for using same for assessing risk of developing SCZ and diagnosing SCZ. Methods for choosing a therapeutic regimen and predicting and/or determining efficacy of a therapeutic regimen based on these genetic markers are also encompassed herein.

26 Claims, 5 Drawing Sheets

(56) References Cited

OTHER PUBLICATIONS

Abdel-Magid et al., "Inhibitors of Bruton's Tyrosine Kinase (Btk) May Treat Inflammation, Immunological Disorders, and Cancer", 2013, ACS Medicinal Chemistry Letters, 4:690-691.

Jiang et al., "Advances in researches on genes and their pathophysiological implications of schizophrenia", Zhonghua Yi Xue Yi Chuan Xue Za Zhi., Chinese Journal of Medical Genetics, 2004; 21:376-378, Abstract Only.

Abel. et al., "Foetal origins of schizophrenia: testable hypotheses of genetic and environmental influences", Br.J. Psychiatry, 2004, 184:383-385.

Wong et al., Genetic and post-mortem mRNA analysis of the 14-3-3 genes that encode phosphoserine/threonine-binding regulatory proteins in schizophrenia and bipolar disorder, Schizophr. Res., 2005; 78:137-146.

Hsu et al., "Bruton's Tyrosine Kinase mediates platelet receptor-induced generation of microparticles: a potential mechanism for amplification of inflammatory responses in rheumatoid arthritis synovial joints", Immunology Letters, 2013, 150:97-104.

Uckun et al., "Bruton's tyrosine kinase as a molecular target in treatment of leukemias and lymphomas as well as inflammatory disorders and autoimmunity", Expert Opin Ther Patents, 2010, 20:1457-1470.

Jones et al., "Animal models of schizophrenia", British J Pharmacol, 2011, 164:1162-1194.

Marcotte et al., "Animal models of schizophrenia: a critical review", J Psychiatry & Neuroscience, 2001, 26:395-410.

Honigberg et al., "The Bruton tyrosine kinase inhibitor PCI-32765 blocks B-cell activation and is efficacious in models of autoimmune disease and B-cell malignancy", Proc Natl Acad Sci, 2010, 107:13075-13080.

Evans et al., "Clinical Development of AVL-292; A Potent, Selective Covalent Btk Inhibitor for the Treatment of B Cell Malignancies", Blood, ASH Annual Meeting Abstracts, 2011, 118: Abstract 3485.

Malaspina et al., Paternal Factors and Schizophrenia Risk: De Novo Mutations and Imprinting, Schizophr Bull, 2001; 27:379-393.

Bradley-Moore et al., "Modeling the effect of advanced paternal age on progeny behavior in mice", Int Soc Dev Psychob, 35th Annual Meeting, published abstract only.

Malaspina et al., "Schizophrenia risk and paternal age: a potential role for de novo mutations in schizophrenia vulnerability genes", CNS Spectrums, 2002; 7:26-69.

McClay et al., "Genome-wide pharmacogenomic study of neurocognition as an indicator of antipsychotic treatment response in schizophrenia", Neuropsychopharmacology, 2011, 36:616-626.

Arion et al., "Altered expression of regulators of the cortical chloride transporters NKCC1 and KCC2 in schizophrenia", Arch Gen Psychiatry, 2011, 68:21-31.

Xu et al., "Strong association of de novo copy number mutations with sporadic schizophrenia", Nature Genetics, 2008, 40:880-885.

Dufner-Beattie et al., "Generation and characterization of mice lacking the zinc uptake transporter ZIP3", Molecular and Cellular Biology, 2005, 25:5607-5615.

Fukada et al., "The zinc transporter SLC39A13/ZIP13 is required for connective tissue development; its involvement in BMP/TGF-beta signaling pathways", PLoS One, 2008, 3:e3642.

Krishnan et al., "The anti-inflammatory compound BAY-11-7082 is a potent inhibitor of protein tyrosine phosphatases", The FEBS Journal, 2013, 2280:830-2841.

Muller et al., "Inflammation in schizophrenia", Advances in Protein Chemistry and Structural Biology, 2012, 88:49-68.

Pigors et al., "TGM5 mutations impact epidermal differentiation in acral peeling skin syndrome", Journal of Investigative Dermatology, 2012, 132: 2422-2429.

Goriely et al., "Selfish spermatogonial selection: a novel mechanism for association between advanced paternal age and neurodevelopmental disorders", Am J Psychiatry, 2013, 170:599-608.

Van Den Bogaert et al., "The DTNBP1 (dysbindin) gene contributes to schizophrenia, depending on family history of the disease", Am J Hum Genet, 2003, 73:1438-1443.

Adzhubei et al., "Predicting Functional Effect of Human Missense Mutations Using PolyPhen-2", Curr Protoc Hum Genet. Jan. 2013;Chapter 7:Unit7.20. doi: 10.1002/0471142905.hg0720s76.

* cited by examiner

JPSS 16: paternal age 53
Proband male, dx disorganized schizophrenia
Mother bipolar, father healthy, no other family history information Kinase-associated phosphatase, cell cycle control protein Maternal dietary choline deficiency reduces DNA methylation of *CDKN3* in developing hippocampus of mouse fetal brain JPSS 57: paternal age 31
Proband female, dx schizoaffective
Father, mother, 2 brothers, extended family healthy Bruton's tyrosine kinase. Critical to B-cell development.

Activation of BTK important in neuronal differentiation of hippocampal progenitor cells. Also involved in immunoregulation of dendritic cells.

Figure 3

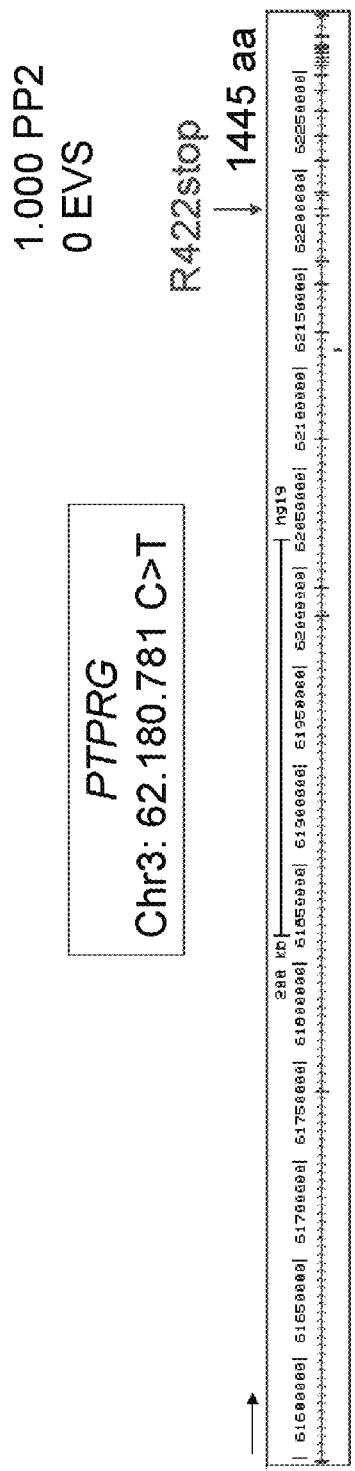

JPSS 52: paternal age 28
Proband male, dx schizoaffective, poly drug dependence
Mother bipolar and cannabis dependent
Father, brother, sister, and extended family healthy Protein tyrosine phosphatase receptor expressed in brain, highest in hippocampus and sensory neurons Over-expression in neuronal cells prevents neurite outgrowth upon treatment with NGF.

Upregulated by cytokines in astrocytoma cells > involved in inflammatory diseases of brain?

JPSS 23: paternal age 34
Proband male, dx paranoid schizophrenia and cannabis dependence
Parents, two brothers, aunts, uncles, grandparents healthy Zinc transporter, 8 transmembrane domains
Highest expression in ganglia and connective tissue

*TGM5*
Chr15: 44.552.271 G>T 1.000 PP2
0 EVS 720 aa

L139I

JPSS 68: paternal age 37
Proband male, dx schizoaffective disorder
Parents healthy Transglutaminase, stabilizes protein structures
Ubiquitously expressed Functions in differentiation of epidermal tissues
Recessive mutations cause acral peeling skin syndrome

SEQUENCE LISTING

```
<160> NUMBER OF SEQ ID NOS: 20

<210> SEQ ID NO 1
<211> LENGTH: 2611
<212> TYPE: DNA
<213> ORGANISM: Homo sapiens

<400> SEQUENCE: 1
aactgagtgg ctgtgaaagg gtggggtttg ctcagactgt ccttcctctc tggactgtaa      60
gaatatgtct ccagggccag tgtctgctgc gatcgagtcc caccttccaa gtcctggcat     120
ctcaatgcat ctgggaagct acctgcatta agtcaggact gagcacacag gtgaactcca     180
gaaagaagaa gctatggccg cagtgattct ggagagcatc tttctgaagc gatcccaaca     240
gaaaaagaaa acatcacctc taaacttcaa gaagcgcctg tttctcttga ccgtgcacaa     300
actctcctac tatgagtatg actttgaacg tgggagaaga ggcagtaaga agggttcaat     360
agatgttgag aagatcactt gtgttgaaac agtggttcct gaaaaaaatc ctcctccaga     420
aagacagatt ccgagaagag gtgaagagtc cagtgaaatg gagcaaattt caatcattga     480
aaggttccct tatcccttcc aggttgtata tgatgaaggg cctctctacg tcttctcccc     540
aactgaagaa ctaaggaagc ggtggattca ccagctcaaa aacgtaatcc ggtacaacag     600
tgatctggtt cagaaatatc acccttgctt ctggatcgat gggcagtatc tctgctgctc     660
tcagacagcc aaaaatgcta tgggctgcca aattttggag aacaggaatg gaagcttaaa     720
```

```
acctgggagt tctcaccgga agacaaaaaa gcctcttccc ccaacgcctg aggaggacca    780
gatcttgaaa aagccactac cgcctgagcc agcagcagca ccagtctcca caagtgagct    840
gaaaaaggtt gtggccctttt atgattacat gccaatgaat gcaaatgatc tacagctgcg   900
gaagggtgat gaatattta tcttggagga aagcaactta ccatggtgga gagcacgaga     960
taaaaatggg caggaaggct acattcctag taactatgtc actgaagcag aagactccat   1020
agaaatgtat gagtggtatt ccaaacacat gactcggagt caggctgagc aactgctaaa   1080
gcaagagggg aaagaaggag gtttcattgt cagagactcc agcaaagctg gcaaatatac   1140
agtgtctgtg tttgctaaat ccacagggga ccctcaaggg gtgatacgtc attatgttgt   1200
gtgttccaca cctcagagcc agtattacct ggctgagaag caccttttca gcaccatccc   1260
tgagctcatt aactaccatc agcacaactc tgcaggactc atatccaggc tcaaatatcc   1320
agtgtctcaa caaaacaaga atgcaccttc cactgcaggc ctgggatacg atcatgggaa   1380
aattgatcca aaggacctga ccttcttgaa ggagctgggg actggacaat ttggggtagt   1440
gaagtatggg aaatggagag gccagtacga cgtggccatc aagatgatca agaaggctc    1500 catgtctgaa gatgaattca ttgaagaagc caaagtcatg atgaatcttt cccatgagaa   1560
gctggtgcag ttgtatggcg tctgcaccaa gcagcgcccc atcttcatca tcactgagta   1620
catggccaat ggctgcctcc tgaactacct gagggagatg cgccaccgct tccagactca   1680
gcagctgcta gagatgtgca aggatgtctg tgaagccatg gaataccctgg agtcaaagca   1740 gttccttcac cgagacctgg cagctcgaaa ctgtttggta aacgatcaag gagttgttaa   1800
agtatctgat ttcggcctgt ccaggtatgt cctggatgat gaatacacaa gctcagtagg   1860
ctccaaattt ccagtccggt ggtccccacc ggaagtcctg atgtatagca agttcagcag   1920
caaatctgac atttgggctt ttggggttt tgatgtggga atttactccc tggggaagat   1980
gccatatgag agatttacta acagtgagac tgctgaacac attgcccaag cctacgtct    2040 ctacaggcct catctggctt cagagaaggt atataccatc atgtacagtt gctggcatga    2100
gaaagcagat gagcgtcca ctttcaaaat tcttctgagc aatattctag atgtcatgga    2160
tgaagaatcc tgagctcgcc aataagcttc ttggttctac ttctcttctc cacaagcccc    2220 aattttcactt tctcagagga aatcccaagc ttaggagccc tggagccttt gtgctcccac    2280
tcaatacaaa aaggcccctc tctacatctg ggaatgcacc tcttctttga ttccctggga    2340
tagtggcttc tgagcaaagg ccaagaaatt attgtgcctg aaatttcccg agagaattaa    2400
gacagactga atttgcgatg aaaatatttt ttaggaggga ggatgtaaat agccgcacaa    2460
aggggtccaa cagctctttg agtaggcatt tggtagagct tgggggtgtg tgtgtggggg    2520
tggaccgaat ttggcaagaa tgaaatggtg tcataaagat gggaggggag ggtgtttttga   2580 taaaataaaa ttactagaaa gcttgaaagt c                                   2611
```

<210> SEQ ID NO 2
<211> LENGTH: 659
<212> TYPE: PRT
<213> ORGANISM: Homo sapiens

<400> SEQUENCE: 2

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg

-continued

```
                35                  40                  45
Arg Gly Ser Lys Lys Gly Ser Ile Asp Val Glu Lys Ile Thr Cys Val
 50                  55                  60
Glu Thr Val Val Pro Glu Lys Asn Pro Pro Glu Arg Gln Ile Pro
 65                  70                  75                  80
Arg Arg Gly Glu Glu Ser Ser Glu Met Glu Gln Ile Ser Ile Ile Glu
                 85                  90                  95
Arg Phe Pro Tyr Pro Phe Gln Val Val Tyr Asp Glu Gly Pro Leu Tyr
                100                 105                 110
Val Phe Ser Pro Thr Glu Glu Leu Arg Lys Arg Trp Ile His Gln Leu
                115                 120                 125
Lys Asn Val Ile Arg Tyr Asn Ser Asp Leu Val Gln Lys Tyr His Pro
                130                 135                 140
Cys Phe Trp Ile Asp Gly Gln Tyr Leu Cys Cys Ser Gln Thr Ala Lys
145                 150                 155                 160
Asn Ala Met Gly Cys Gln Ile Leu Glu Asn Arg Asn Gly Ser Leu Lys
                165                 170                 175
Pro Gly Ser Ser His Arg Lys Thr Lys Lys Pro Leu Pro Pro Thr Pro
                180                 185                 190
Glu Glu Asp Gln Ile Leu Lys Lys Pro Leu Pro Pro Glu Pro Ala Ala
                195                 200                 205
Ala Pro Val Ser Thr Ser Glu Leu Lys Lys Val Val Ala Leu Tyr Asp
210                 215                 220
Tyr Met Pro Met Asn Ala Asn Asp Leu Gln Leu Arg Lys Gly Asp Glu
225                 230                 235                 240
Tyr Phe Ile Leu Glu Glu Ser Asn Leu Pro Trp Trp Arg Ala Arg Asp
                245                 250                 255
Lys Asn Gly Gln Glu Gly Tyr Ile Pro Ser Asn Tyr Val Thr Glu Ala
                260                 265                 270
Glu Asp Ser Ile Glu Met Tyr Glu Trp Tyr Ser Lys His Met Thr Arg
                275                 280                 285
Ser Gln Ala Glu Gln Leu Leu Lys Gln Glu Gly Lys Glu Gly Gly Phe
                290                 295                 300
Ile Val Arg Asp Ser Ser Lys Ala Gly Lys Tyr Thr Val Ser Val Phe
305                 310                 315                 320
Ala Lys Ser Thr Gly Asp Pro Gln Gly Val Ile Arg His Tyr Val Val
                325                 330                 335
Cys Ser Thr Pro Gln Ser Gln Tyr Tyr Leu Ala Glu Lys His Leu Phe
                340                 345                 350
Ser Thr Ile Pro Glu Leu Ile Asn Tyr His Gln His Asn Ser Ala Gly
                355                 360                 365
Leu Ile Ser Arg Leu Lys Tyr Pro Val Ser Gln Gln Asn Lys Asn Ala
                370                 375                 380
Pro Ser Thr Ala Gly Leu Gly Tyr Gly Ser Trp Glu Ile Asp Pro Lys
385                 390                 395                 400
Asp Leu Thr Phe Leu Lys Glu Leu Gly Thr Gly Gln Phe Gly Val Val
                405                 410                 415
Lys Tyr Gly Lys Trp Arg Gly Gln Tyr Asp Val Ala Ile Lys Met Ile
                420                 425                 430
Lys Glu Gly Ser Met Ser Glu Asp Glu Phe Ile Glu Glu Ala Lys Val
                435                 440                 445
Met Met Asn Leu Ser His Glu Lys Leu Val Gln Leu Tyr Gly Val Cys
450                 455                 460
```

Thr Lys Gln Arg Pro Ile Phe Ile Thr Glu Tyr Met Ala Asn Gly
465                 470                 475                 480

Cys Leu Leu Asn Tyr Leu Arg Glu Met Arg His Arg Phe Gln Thr Gln
            485                 490                 495

Gln Leu Leu Glu Met Cys Lys Asp Val Cys Glu Ala Met Glu Tyr Leu
        500                 505                 510

Glu Ser Lys Gln Phe Leu His Arg Asp Leu Ala Ala Arg Asn Cys Leu
    515                 520                 525

Val Asn Asp Gln Gly Val Val Lys Val Ser Asp Phe Gly Leu Ser Arg
530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
            565                 570                 575

Lys Ser Asp Ile Trp Ala Phe Gly Val Leu Met Trp Glu Ile Tyr Ser
        580                 585                 590

Leu Gly Lys Met Pro Tyr Glu Arg Phe Thr Asn Ser Glu Thr Ala Glu
    595                 600                 605

His Ile Ala Gln Gly Leu Arg Leu Tyr Arg Pro His Leu Ala Ser Glu
610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
            645                 650                 655

Glu Glu Ser

<210> SEQ ID NO 3
<211> LENGTH: 786
<212> TYPE: DNA
<213> ORGANISM: Homo sapiens

<400> SEQUENCE: 3
acagaaggac gaaccagtga gctaagctgc ggggcgcggg ctcggccggg gcaccggtga      60
gtcgccggcg ctgcagaggg aggcggcact ggtctcgacg tggggcggcc agcgatgaag     120
ccgcccagtt caatacaaac aagttgtaaa tttaaagatg ttagaagaaa tgtccaaaaa     180
gatacagaag aactaaagag ctgtggtata caagacatat ttgttttctg caccagaggg     240
gaactgtcaa aatatagagt cccaaacctt ctggatctct accagcaatg tggaattatc     300
acccatcatc atccaatcgc agatggaggg actcctgaca tagccagctg ctgtgaaata     360
atggaagagc ttacaacctg ccttaaaaat taccgaaaaa ccttaataca ctgctatgga     420
ggacttggga gatcttgtct tgtagctgct tgtctcctac tatacctgtc tgacacaata     480
tcaccagagc aagccataga cagcctgcga gacctaagag gatccgggc aatacagacc     540
atcaagcaat acaattatct tcatgagttt cgggacaaat tagctgcaca tctatcatca     600
agagattcac aatcaagatc tgtatcaaga taaaggaatt caaatagcat atatatgacc     660
atgtctgaaa tgtcagttct ctagcataat ttgtattgaa atgaaaccac cagtgttatc     720
aacttgaatg taaatgtaca tgtgcagata ttcctaaagt tttattgaca aaaaaaaaa     780
aaaaaa                                                                786

<210> SEQ ID NO 4
<211> LENGTH: 172
<212> TYPE: PRT

<213> ORGANISM: Homo sapiens

<400> SEQUENCE: 4

```
Met Lys Pro Pro Ser Ser Ile Gln Thr Ser Cys Lys Phe Lys Asp Val
1               5                   10                  15
Arg Arg Asn Val Gln Lys Asp Thr Glu Glu Leu Lys Ser Cys Gly Ile
            20                  25                  30
Gln Asp Ile Phe Val Phe Cys Thr Arg Gly Glu Leu Ser Lys Tyr Arg
        35                  40                  45
Val Pro Asn Leu Leu Asp Leu Tyr Gln Gln Cys Gly Ile Ile Thr His
    50                  55                  60
His His Pro Ile Ala Asp Gly Gly Thr Pro Asp Ile Ala Ser Cys Cys
65                  70                  75                  80
Glu Ile Met Glu Glu Leu Thr Thr Cys Leu Lys Asn Tyr Arg Lys Thr
                85                  90                  95
Leu Ile His Cys Tyr Gly Gly Leu Gly Arg Ser Cys Leu Val Ala Ala
            100                 105                 110
Cys Leu Leu Leu Tyr Leu Ser Asp Thr Ile Ser Pro Glu Gln Ala Ile
        115                 120                 125
Asp Ser Leu Arg Asp Leu Arg Gly Ser Gly Ala Ile Gln Thr Ile Lys
    130                 135                 140
Gln Tyr Asn Tyr Leu His Glu Phe Arg Asp Lys Leu Ala Ala His Leu
145                 150                 155                 160
Ser Ser Arg Asp Ser Gln Ser Arg Ser Val Ser Arg
                165                 170
```

<210> SEQ ID NO 5
<211> LENGTH: 6648
<212> TYPE: DNA
<213> ORGANISM: Homo sapiens

<400> SEQUENCE: 5

```
acatgttact tcctgtatgg aggcatggcc agtttccagc ccgcgctct tcgttccttc      60
ccagcctgcg ccggagccac aactttcagg agcatggact gaaggcgccc tcgccccagc   120
gcccctctga gatcctttgt gttttcctcc gtttcctccg gccgtttcta ttttgggggg   180
ctctccgctc ccctgcctc tcccctcccc ttcccctctc gcaaacatgc ctccttcctt    240
cccggggccc tggaaggagc tgcctgcctg aagcccggag acgccgcgcc gcgctcagcc   300
ccgccgccgc ccgccggctc tcgggctgtg ctgcgctgcc gactcaagtt ggggatcctc    360
ggctgctcgc cgccgccgcc gcggtccct gcctgcccca ggcccggggc atcgccgccg    420
gccgccgact ccgcgccctg cccgatcggc tctctccttt ttaaacggaa agcagccttt    480
ctccgccgag aggatcgtcc ccagcgtggc tctgcgttcc cggtcacttt ttgagatttt    540
ccggggggcg ctcggcggct tcccggattc aagggggact cgggccgccg agcgcggggg    600
gcccgtggag cgggcgagcc ggggaagcgc ccggcttag cggaggctcg cacgaggca     660
agaacttatt caacaagttt acctccctgc tttcctcttt tcgatgtgcg ttttcggaca    720
tgcggaggtt actggaaccg tgttggtgga ttttgttcct gaaaatcacc agttccgtgc    780
tccattatgt cgtgtgcttc cccgcgttga cagaaggcta cgttgggcc ctgcacgaga     840
atagacacgg cagcgcagtg cagatccgca ggcgcaaggc ttcaggcgac ccgtactggg    900
cctactctgg tgcctatggt cctgagcact gggtcacgtc tagtgtcagc gtgggggcc    960
gtcaccagtc tcctattgac attttagacc agtatgcgcg tgttggggaa gaataccagg   1020
```

```
aactgcaact cgatggcttc gacaatgagt cttctaacaa aacctggatg aaaaacacag   1080
ggaaaacagt cgccatcctt ctgaaagacg actattttgt cagtggagct ggtctacctg   1140
gcagattcaa agctgagaag gtggaatttc actggggcca cagcaatggc tcagcgggct   1200
ctgaacacag catcaatggc aggaggtttc ctgttgagat gcagattttc ttttacaatc   1260
cagatgactt tgacagcttt caaaccgcaa tttctgagaa cagaataatc ggagccatgg   1320
ccatattttt tcaagtcagt ccgagggaca attctgcact ggatcctatt atccacgggt   1380
tgaagggtgt cgtacatcat gagaaggaga cctttctgga tcctttcgtc ctccgggacc   1440
tcctgcctgc atccctgggc agctattatc ggtacacagg ttccttgacc acaccaccgt   1500
gtagcgaaat agtggagtgg atagtcttcc ggagacccgt ccccatctct taccatcagc   1560
ttgaggcttt ttattccatc ttcaccacgg agcagcaaga ccatgtcaag tcggtggagt   1620
atctgagaaa taactttcga ccacagcagc gtctgcatga cagggtggtg tccaagtccg   1680
ccgtccgtga ctcctggaac cacgacatga cagacttctt agaaaaccca ctggggacag   1740
aagcctctaa agtttgcagc tctccaccca tccacatgaa ggtgcagcct ctgaaccaga   1800
cggcactgca ggtgtcctgg agccagccgg agactatcta ccacccaccc atcatgaact   1860
acatgatctc ctacagctgg accaagaatg aggacgagaa ggagaagacg tttacaaagg   1920
acagcgacaa agacttgaaa gccaccatta gccatgtctc acccgatagc cttttacctgt   1980 tccgagtcca ggccgtgtgt cggaacgaca tgcgcagcga cttttagccag acgatgctgt   2040 ttcaagctaa taccactcga atattccaag ggaccagaat agtgaaaaca ggagtgccca   2100
cagcgtctcc tgcctcttca gccgacatgg cccccatcag ctcggggtct tctacctgga   2160
cgtcctctgg catcccattc tcatttgttt ccatggcaac tgggatgggc cctcctcca   2220 gtggcagcca ggccacagtg gcctcggtgg tcaccagcac gctgctcgcc ggcctggggt   2280
tcggcggtgg tggcatctcc tctttcccca gcactgtgtg gcccacgcgc ctcccgacgg   2340
ccgcctcagc cagcaagcag gcggctaggc cagtcctagc caccacagag gccttggctt   2400
ctccagggcc cgatggtgat cgtcaccaa ccaaggacgg cgagggcacc gaggaaggag   2460
agaaggatga gaaaagcgag agtgaggatg gggagcggga gcacgaggag gatggagaga   2520
aggactccga aaagaaggag aagagtgggg tgacccacgc tgccgaggag cggaatcaga   2580
cggagcccag ccccacaccc tcgtctccta acaggactgc cgagggaggg catcagacta   2640
tacctgggca tgagcaggat cacactgccg tccccacaga ccagacgggc ggaaggaggg   2700
atgccggccc aggcctggac cccgacatgg tcacctccac ccaagtgccc cccaccgcca   2760
cagaggagca gtatgcaggg agtgatccca agaggcccga aatgccatct aaaaagccta   2820
tgtcccgcgg ggaccgattt tctgaagaca gcagatttat cactgttaat ccagcggaaa   2880
aaaacacctc tggaatgata agccgccctg ctccagggag gatggagtgg atcatccctc   2940
tgattgtggt atcagccttg accttcgtgt gcctcatcct tctcattgct gtgctcgttt   3000
actggagagg gtgtaacaaa ataaagtcca agggctttcc cagacgtttc cgtgaagtgc   3060
cttcttctgg ggagagagga gagaagggga gcagaaaatg ttttcagact gctcatttct   3120
atgtggaaga cagcagttca cctcgagtgg tccctaatga agtatccct attattccta   3180 ttccggatga catggaagcc attcctgtca aacagtttgt caaacacatc ggtgagctct   3240
attctaataa ccagcatggg ttctctgagg attttgagga agtccagcgc tgtactgctg   3300
atatgaacat cactgcagag cattccaatc atccagaaaa caagcacaaa acagatacaa   3360
tcaacatttt agcatatgat cacagtaggg tgaagttaag accttaccca ggaaaagact   3420
```

```
ctaagcacag cgactacatt aatgcaaact atgttgatgg ttacaacaaa gcaaaagcct    3480
acattgccac ccaaggacct ttgaagtcta catttgaaga tttctggagg atgatttggg    3540
aacaaaacac tggaatcatt gtgatgatta cgaaccttgt ggaaaaagga agacgaaaat    3600
gtgatcagta ttggccaaca gagaacagtg aggaatatgg aaacattatt gtcacgctga    3660
agagcacaaa aatacatgcc tgctacactg ttcgtcgttt ttcaatcaga aatacaaaag    3720
tgaaaagggg tcagaaggga aatcccaagg gtcgtcagaa tgaaagggta gtgatccagt    3780
atcactatac acagtggcct gacatgggag ttcccgagta tgcccttcca gtactgactt    3840
tcgtgaggag atcctcagca gctcggatgc cagaaacggg ccctgtgttg gtgcactgca    3900
gtgctggtgt gggcagaaca ggcacctata ttgtaataga cagcatgctg caacagataa    3960
aagacaaaag cacagttaac gtcctgggat tcctgaagca tatcaggaca cagcgtaact    4020
acctcgtcca gactgaggag cagtacattt tcatccatga tgccttgttg gaagccattc    4080
ttggaaagga gactgaagta tcttcaaatc agctgcacag ctatgttaac agcatcctta    4140
taccaggagt aggaggaaag acacgactgg aaaagcaatt caagctggtc acacagtgta    4200
atgcaaaata tgtggaatgt ttcagtgctc agaaagagtg taacaaagaa aagaacagaa    4260
actcttcagt tgtgccatct gagcgtgctc gagtgggtct tgcaccattg cctggaatga    4320
aaggaacaga ttacattaat gcttcttata tcatgggcta ttataggagc aatgaattta    4380
ttataactca gcatcctctg ccacatacta cgaaagattt ctggcgaatg atttgggatc    4440
ataacgcaca gatcattgtc atgctgccag acaaccagag cttggcagaa gatgagtttg    4500
tgtactggcc aagtcgagaa gaatccatga actgtgaggc ctttaccgtc acccttatca    4560
gcaaagacag actgtgcctc tctaatgaag aacaaattat catccatgac tttatccttg    4620
aagctacaca ggatgactat gtcttagaag ttcggcactt tcagtgtccc aaatggccta    4680
acccagatgc ccccataagt agtaccttttg aacttatcaa cgtcatcaag gaagaggcct    4740
taacaaggga tggtcccacc attgttcatg atgagtatgg agcagtttca gcaggaatgt    4800
tatgtgccct taccccctg tcccagcaac tggagaatga aaatgctgtg gatgttttcc    4860
aggttgcaaa aatgatcaat cttatgaggc ctggagtatt cacagacatt gaacaatacc    4920
agttcatcta taaagcaatg cttagcttgg tcagcactaa agaaaatgga aatggtccca    4980
tgacagtaga caaaaatggt gctgttctta ttgcagatga atcagaccct gctgagagca    5040
tggagtccct agtgtgactg gaatcctgaa agggcactta atttgtaaac ttctgaagac    5100
tgagaacttt ttttgaggcct tttttgccag actctaggtt atacaataac ccagttactt    5160
ttttacactg ataaaagttt tgatatttat tttttgccat tttatgtctt aatggtatcc    5220
tactgagcat ttgcacctct gttcatttca cacagtgaaa cgcaatttta cctagtttgc    5280
actatatgat cagtgttact gcctataatc ttatacaaca gcaaaccctg atgtgacatt    5340
ccatgacgac atacatgcta ctttttttta gttcaataca gtgaaggtct ttgttatgac    5400
agtgaatatt gcttttatta ttattattgc tgaagtggtt gcattctact agcaggcaat    5460
gctgtacttt tcttcagtcc tcctctcctt tttattttag gcactgttca atactgtatg    5520
ccttctgtat tttaatggag tggatagcat tgttttcttt tacagactag caggctactg    5580
ggacctaaaa aggtctgtta atgtcatggc cttgaaacag ttccatttat gctggttaag    5640
agatccctta agaagttaga aggcttaaga actgcttcat gtgaacatcc cttattagtt    5700
acaaagttat attcacagtt ttttaaaaat gtgtcaaaat aaaggataac tctgtattac    5760
```

-continued

```
agcttttcaca gtagctatgt ggacaatgtg ttatttccat tttgactctc taaaatagct    5820
acatcctaaa atcagggcta tctttaacaa tagcaagata gcaatattat atacaactca    5880
gttatgagac cctttagtta ttctccatta atgcttctta gtttgtaata ccatacctca    5940
cagtaggtag aagaatgaaa acttctgcag gtgtgtaatt ttgaaactag tcctctaaaa    6000
attccctatt actcctatag caatctaata aaaactacct acatagttac tgttttcttt    6060
ccttctttgc caaatgtttt ataataaatc tcttaattac atacattttt ctacttaaga    6120
ttaaattgga aatactgtct tagcaaaagt cttgggacta tctaaactcc cacacataga    6180
taaatctgat ttggagagag aaatttaaaa tatttaatta aaggtgatac ccacatttc    6240 aagttttaa aagagggaga tggctttgta tgcttttgtg tagtttagaa cagatacaca    6300
ttagtaaaag ataccaataa tcattagagc tcaaggaagt tattaggtgc agcctctgga    6360
gccatactca cgctgcagtg cataatggga aaattaggag cattaataag aaatttcagt    6420
agtgtttgta aggaaaataa gctacttact gagatctgtt tcttctattg catgtttgct    6480
tttgagggac agcttctgtc aaaagtgaaa tcatcaccag aactgggcct gttaggaaga    6540
atagggtttt atttactttt tatgtcaatt aacttcaaca aaaaggccac gctggctgct    6600
gtcatgccat ctgggtatgc attaaacatt aatgatgatc agcactga                 6648
```

<210> SEQ ID NO 6
<211> LENGTH: 1445
<212> TYPE: PRT
<213> ORGANISM: Homo sapiens

<400> SEQUENCE: 6

```
Met Arg Arg Leu Leu Glu Pro Cys Trp Trp Ile Leu Phe Leu Lys Ile
 1               5                  10                  15

Thr Ser Ser Val Leu His Tyr Val Val Cys Phe Pro Ala Leu Thr Glu
             20                  25                  30

Gly Tyr Val Gly Ala Leu His Glu Asn Arg His Gly Ser Ala Val Gln
         35                  40                  45

Ile Arg Arg Lys Ala Ser Gly Asp Pro Tyr Trp Ala Tyr Ser Gly
     50                  55                  60

Ala Tyr Gly Pro Glu His Trp Val Thr Ser Val Ser Cys Gly Gly
 65                  70                  75                  80

Arg His Gln Ser Pro Ile Asp Ile Leu Asp Gln Tyr Ala Arg Val Gly
                 85                  90                  95

Glu Glu Tyr Gln Glu Leu Gln Leu Asp Gly Phe Asp Asn Glu Ser Ser
            100                 105                 110

Asn Lys Thr Trp Met Lys Asn Thr Gly Lys Thr Val Ala Ile Leu Leu
        115                 120                 125

Lys Asp Asp Tyr Phe Val Ser Gly Ala Gly Leu Pro Gly Arg Phe Lys
    130                 135                 140

Ala Glu Lys Val Glu Phe His Trp Gly His Ser Asn Gly Ser Ala Gly
145                 150                 155                 160

Ser Glu His Ser Ile Asn Gly Arg Arg Phe Pro Val Glu Met Gln Ile
                165                 170                 175

Phe Phe Tyr Asn Pro Asp Asp Phe Asp Ser Gln Thr Ala Ile Ser
            180                 185                 190

Glu Asn Arg Ile Ile Gly Ala Met Ala Ile Phe Phe Gln Val Ser Pro
        195                 200                 205

Arg Asp Asn Ser Ala Leu Asp Pro Ile Ile His Gly Leu Lys Gly Val
    210                 215                 220
```

```
Val His His Glu Lys Glu Thr Phe Leu Asp Pro Phe Val Leu Arg Asp
225                 230                 235                 240

Leu Leu Pro Ala Ser Leu Gly Ser Tyr Tyr Arg Tyr Thr Gly Ser Leu
                245                 250                 255

Thr Thr Pro Pro Cys Ser Glu Ile Val Glu Trp Ile Val Phe Arg Arg
            260                 265                 270

Pro Val Pro Ile Ser Tyr His Gln Leu Glu Ala Phe Tyr Ser Ile Phe
        275                 280                 285

Thr Thr Glu Gln Gln Asp His Val Lys Ser Val Glu Tyr Leu Arg Asn
    290                 295                 300

Asn Phe Arg Pro Gln Arg Leu His Asp Arg Val Val Ser Lys Ser
305                 310                 315                 320

Ala Val Arg Asp Ser Trp Asn His Asp Met Thr Asp Phe Leu Glu Asn
                325                 330                 335

Pro Leu Gly Thr Glu Ala Ser Lys Val Cys Ser Ser Pro Ile His
            340                 345                 350

Met Lys Val Gln Pro Leu Asn Gln Thr Ala Leu Gln Val Ser Trp Ser
        355                 360                 365

Gln Pro Glu Thr Ile Tyr His Pro Pro Ile Met Asn Tyr Met Ile Ser
370                 375                 380

Tyr Ser Trp Thr Lys Asn Glu Asp Glu Lys Glu Lys Thr Phe Thr Lys
385                 390                 395                 400

Asp Ser Asp Lys Asp Leu Lys Ala Thr Ile Ser His Val Ser Pro Asp
                405                 410                 415

Ser Leu Tyr Leu Phe Arg Val Gln Ala Val Cys Arg Asn Asp Met Arg
            420                 425                 430

Ser Asp Phe Ser Gln Thr Met Leu Phe Gln Ala Asn Thr Thr Arg Ile
        435                 440                 445

Phe Gln Gly Thr Arg Ile Val Lys Thr Gly Val Pro Thr Ala Ser Pro
450                 455                 460

Ala Ser Ser Ala Asp Met Ala Pro Ile Ser Ser Gly Ser Ser Thr Trp
465                 470                 475                 480

Thr Ser Ser Gly Ile Pro Phe Ser Phe Val Ser Met Ala Thr Gly Met
            485                 490                 495

Gly Pro Ser Ser Ser Gly Ser Gln Ala Thr Val Ala Ser Val Val Thr
        500                 505                 510

Ser Thr Leu Leu Ala Gly Leu Gly Phe Gly Gly Gly Ile Ser Ser
    515                 520                 525

Phe Pro Ser Thr Val Trp Pro Thr Arg Leu Pro Thr Ala Ala Ser Ala
530                 535                 540

Ser Lys Gln Ala Ala Arg Pro Val Leu Ala Thr Thr Glu Ala Leu Ala
545                 550                 555                 560

Ser Pro Gly Pro Asp Gly Asp Ser Ser Pro Thr Lys Asp Gly Glu Gly
                565                 570                 575

Thr Glu Glu Gly Glu Lys Asp Glu Ser Glu Ser Glu Asp Gly Glu
            580                 585                 590

Arg Glu His Glu Glu Asp Gly Glu Lys Asp Ser Glu Lys Lys Glu Lys
        595                 600                 605

Ser Gly Val Thr His Ala Ala Glu Glu Arg Asn Gln Thr Glu Pro Ser
    610                 615                 620

Pro Thr Pro Ser Ser Pro Asn Arg Thr Ala Glu Gly Gly His Gln Thr
625                 630                 635                 640
```

-continued

```
Ile Pro Gly His Glu Gln Asp His Thr Ala Val Pro Thr Asp Gln Thr
                645                 650                 655
Gly Gly Arg Arg Asp Ala Gly Pro Gly Leu Asp Pro Asp Met Val Thr
        660                 665                 670
Ser Thr Gln Val Pro Pro Thr Ala Thr Glu Glu Gln Tyr Ala Gly Ser
    675                 680                 685
Asp Pro Lys Arg Pro Glu Met Pro Ser Lys Lys Pro Met Ser Arg Gly
690                 695                 700
Asp Arg Phe Ser Glu Asp Ser Arg Phe Ile Thr Val Asn Pro Ala Glu
705                 710                 715                 720
Lys Asn Thr Ser Gly Met Ile Ser Arg Pro Ala Pro Gly Arg Met Glu
                725                 730                 735
Trp Ile Ile Pro Leu Ile Val Val Ser Ala Leu Thr Phe Val Cys Leu
            740                 745                 750
Ile Leu Leu Ile Ala Val Leu Val Tyr Trp Arg Gly Cys Asn Lys Ile
        755                 760                 765
Lys Ser Lys Gly Phe Pro Arg Arg Phe Arg Glu Val Pro Ser Ser Gly
    770                 775                 780
Glu Arg Gly Glu Lys Gly Ser Arg Lys Cys Phe Gln Thr Ala His Phe
785                 790                 795                 800
Tyr Val Glu Asp Ser Ser Ser Pro Arg Val Val Pro Asn Glu Ser Ile
                805                 810                 815
Pro Ile Ile Pro Ile Pro Asp Asp Met Glu Ala Ile Pro Val Lys Gln
            820                 825                 830
Phe Val Lys His Ile Gly Glu Leu Tyr Ser Asn Asn Gln His Gly Phe
        835                 840                 845
Ser Glu Asp Phe Glu Glu Val Gln Arg Cys Thr Ala Asp Met Asn Ile
    850                 855                 860
Thr Ala Glu His Ser Asn His Pro Glu Asn Lys His Lys Asn Arg Tyr
865                 870                 875                 880
Ile Asn Ile Leu Ala Tyr Asp His Ser Arg Val Lys Leu Arg Pro Leu
                885                 890                 895
Pro Gly Lys Asp Ser Lys His Ser Asp Tyr Ile Asn Ala Asn Tyr Val
            900                 905                 910
Asp Gly Tyr Asn Lys Ala Lys Ala Tyr Ile Ala Thr Gln Gly Pro Leu
        915                 920                 925
Lys Ser Thr Phe Glu Asp Phe Trp Arg Met Ile Trp Glu Gln Asn Thr
    930                 935                 940
Gly Ile Ile Val Met Ile Thr Asn Leu Val Glu Lys Gly Arg Arg Lys
945                 950                 955                 960
Cys Asp Gln Tyr Trp Pro Thr Glu Asn Ser Glu Glu Tyr Gly Asn Ile
                965                 970                 975
Ile Val Thr Leu Lys Ser Thr Lys Ile His Ala Cys Tyr Thr Val Arg
            980                 985                 990
Arg Phe Ser Ile Arg Asn Thr Lys Val Lys Lys Gly Gln Lys Gly Asn
        995                 1000                1005
Pro Lys Gly Arg Gln Asn Glu Arg Val Val Ile Gln Tyr His Tyr Thr
    1010                1015                1020
Gln Trp Pro Asp Met Gly Val Pro Glu Tyr Ala Leu Pro Val Leu Thr
1025                1030                1035                1040
Phe Val Arg Arg Ser Ser Ala Ala Arg Met Pro Glu Thr Gly Pro Val
                1045                1050                1055
Leu Val His Cys Ser Ala Gly Val Gly Arg Thr Gly Thr Tyr Ile Val
```

1060                1065                1070
Ile Asp Ser Met Leu Gln Gln Ile Lys Asp Lys Ser Thr Val Asn Val
            1075                1080                1085

Leu Gly Phe Leu Lys His Ile Arg Thr Gln Arg Asn Tyr Leu Val Gln
        1090                1095                1100

Thr Glu Glu Gln Tyr Ile Phe Ile His Asp Ala Leu Leu Glu Ala Ile
1105                1110                1115                1120

Leu Gly Lys Glu Thr Glu Val Ser Ser Asn Gln Leu His Ser Tyr Val
                1125                1130                1135

Asn Ser Ile Leu Ile Pro Gly Val Gly Gly Lys Thr Arg Leu Glu Lys
            1140                1145                1150

Gln Phe Lys Leu Val Thr Gln Cys Asn Ala Lys Tyr Val Glu Cys Phe
        1155                1160                1165

Ser Ala Gln Lys Glu Cys Asn Lys Glu Lys Asn Arg Asn Ser Ser Val
    1170                1175                1180

Val Pro Ser Glu Arg Ala Arg Val Gly Leu Ala Pro Leu Pro Gly Met
1185                1190                1195                1200

Lys Gly Thr Asp Tyr Ile Asn Ala Ser Tyr Ile Met Gly Tyr Tyr Arg
                1205                1210                1215

Ser Asn Glu Phe Ile Ile Thr Gln His Pro Leu Pro His Thr Thr Lys
            1220                1225                1230

Asp Phe Trp Arg Met Ile Trp Asp His Asn Ala Gln Ile Ile Val Met
        1235                1240                1245

Leu Pro Asp Asn Gln Ser Leu Ala Glu Asp Glu Phe Val Tyr Trp Pro
    1250                1255                1260

Ser Arg Glu Glu Ser Met Asn Cys Glu Ala Phe Thr Val Thr Leu Ile
1265                1270                1275                1280

Ser Lys Asp Arg Leu Cys Leu Ser Asn Glu Glu Gln Ile Ile Ile His
                1285                1290                1295

Asp Phe Ile Leu Glu Ala Thr Gln Asp Asp Tyr Val Leu Glu Val Arg
            1300                1305                1310

His Phe Gln Cys Pro Lys Trp Pro Asn Pro Asp Ala Pro Ile Ser Ser
        1315                1320                1325

Thr Phe Glu Leu Ile Asn Val Ile Lys Glu Glu Ala Leu Thr Arg Asp
    1330                1335                1340

Gly Pro Thr Ile Val His Asp Glu Tyr Gly Ala Val Ser Ala Gly Met
1345                1350                1355                1360

Leu Cys Ala Leu Thr Thr Leu Ser Gln Gln Leu Glu Asn Glu Asn Ala
                1365                1370                1375

Val Asp Val Phe Gln Val Ala Lys Met Ile Asn Leu Met Arg Pro Gly
            1380                1385                1390

Val Phe Thr Asp Ile Glu Gln Tyr Gln Phe Ile Tyr Lys Ala Met Leu
        1395                1400                1405

Ser Leu Val Ser Thr Lys Glu Asn Gly Asn Gly Pro Met Thr Val Asp
    1410                1415                1420

Lys Asn Gly Ala Val Leu Ile Ala Asp Glu Ser Asp Pro Ala Glu Ser
1425                1430                1435                1440

Met Glu Ser Leu Val
            1445

<210> SEQ ID NO 7
<211> LENGTH: 2429
<212> TYPE: DNA
<213> ORGANISM: Homo sapiens

<400> SEQUENCE: 7

```
ggcgcctcgg gttccggaca ggccccttgt gacgtggccg cgcgccgggg gcggccccgg      60
gccgggggcc gggcggccgg gcggccgggc ggggcagagc ctgggcgggg cgcggcaccg     120
cagctggatg gctggggccg cccggatcgc cgccgccgcc gccgcacgta cgtggcatgc     180
ctggatgtcc ctgccctggc tgtggcatgg cgggcccaag gctcctcttc ctcactgccc     240
ttgccctgga gctcttggga agggctgggg gttcccagcc ggcctccgg agccggggga      300
ctgcgacggc ctgtcgcctg acaacaagg aaagcgagtc ctgggggct ctgctgagcg       360
gagagcggct ggacacctgg atctgctccc tcctgggttc cctcatggtg gggctcagtg     420
gggtcttccc gttgcttgtc attccctag agatggggac catgctgcgc tcagaagctg      480
gggcctggcg cctgaagcag ctgctcagct tcgccctggg gggactcttg gcaatgtgt      540
ttctgcatct gctgcccgaa gcctgggcct acacgtgcag cgccagccct ggtggtgagg     600
ggcagagcct gcagcagcag caacagctgg ggctgtgggt cattgctggc atcctgacct     660
tcctggcgtt ggagaagatg ttcctggaca gcaaggagga ggggaccagc caggccccca    720
acaaagaccc cactgctgct gccgccgcgc tcaatggagg ccactgtctg gcccagccgg    780
ctgcagagcc cggcctcggt gccgtggtcc ggagcatcaa agtcagcggc tacctcaacc    840
tgctggccaa caccatcgat aacttcaccc acgggctggc tgtggctgcc agcttccttg    900
tgagcaagaa gatcgggctc ctgacaacca tggccatcct cctgcatgag atccccatg     960
aggtgggcga ctttgccatc ctgctccggg ccggctttga ccgatggagc gcagccaagc    1020
tgcaactctc aacagcgctg gggggcctac tgggcgctgg cttcgccatc tgtacccagt    1080
cccccaaggg agtagttggg tgttctcccg ctgcagagga gacggcagcc tgggtcctgc    1140
ccttcacctc tggcggcttt ctctacatcg ccttggtgaa cgtgctccct gacctcttgg    1200
aagaagagga cccgtggcgc tccctgcagc agctgcttct gctctgtgcg ggcatcgtgg    1260
taatggtgct gttctcgctc ttcgtggatt aactttccct gatgccgacg ccctgcccc     1320
ctgcagcaat aagatgctcg gattcactct gtgaccgcat atgtgagagg cagagagggc    1380
gagtggctgc gagagagaat gagcctcccg ccagacagga gggaggtgcg tgtggatgta    1440
tgtggtgtgc acatgtggcc agaggtgtgt gcgcgagacc gacactgtga tccctgtgct    1500
gggtccgggg cccagtgtag cgcctgtccc cagccatgct gtggttacct ctccttgccg    1560
ccctgtcacc ttcacctccc ggagtaagca gcgaggaaga gcagcactgg tcccaagcag    1620
aggccttgcc ctgctgggac cccgggagtg agagcagccc aaggatccag ggtgcaggga    1680
actccagagc tgcccacctc ccactgcccc ctcagcacac acacagtccc caggcggcct    1740
aggggccaag gctggggcgg ctttggtccc ttttcctggc ccttccttcc ccacttctaa    1800
gccaaagaaa ggagaggcag gtgctcctgt accccagccc cactcagcac tgacagtccc    1860
cagctcctag tagtgagctg ggaggcgctt cctaagaccc tttcctcagg gctgccctgg    1920
gagctcattc ctggccaaca cgccctggca gcaccagcag ctcttgccac ctccagctgc    1980
caaacagcag cctgccgggc agggagcagc cccaggccag agaggcctcc cggtccagct    2040
cagggatgct cctgccagca caggggccag ggactcctgg agcaggcaca tagtgagccc    2100
gggcagccct gcccagctca ggccccttt cttccccatt gaggttgggg taggtgggg     2160
cggtgagggc tccacgttgt cagcgctcag gaatgtgctc cggcagagtg ctgaagccat    2220
aatccccaac catttcccctt ggctgacgcc caggtactca gctggcccac tccacagcca    2280
```

```
ggcctggccc tgcccttcac cgtggatgtt ttcagaagtg gccatcgaga ggtctggatg    2340
gttttatagc aactttgctg tgattccgtt tgtatctgta aatatttgtt ctatagataa    2400
gatacaaata aatattatcc acatactgg                                       2429
```

<210> SEQ ID NO 8
<211> LENGTH: 371
<212> TYPE: PRT
<213> ORGANISM: Homo sapiens

<400> SEQUENCE: 8

```
Met Pro Gly Cys Pro Cys Pro Gly Cys Gly Met Ala Gly Pro Arg Leu
 1               5                  10                  15

Leu Phe Leu Thr Ala Leu Ala Leu Glu Leu Leu Gly Arg Ala Gly Gly
            20                  25                  30

Ser Gln Pro Ala Leu Arg Ser Arg Gly Thr Ala Thr Ala Cys Arg Leu
        35                  40                  45

Asp Asn Lys Glu Ser Glu Ser Trp Gly Ala Leu Leu Ser Gly Glu Arg
    50                  55                  60

Leu Asp Thr Trp Ile Cys Ser Leu Gly Ser Leu Met Val Gly Leu
65                  70                  75                  80

Ser Gly Val Phe Pro Leu Leu Val Ile Pro Leu Glu Met Gly Thr Met
                85                  90                  95

Leu Arg Ser Glu Ala Gly Ala Trp Arg Leu Lys Gln Leu Leu Ser Phe
            100                 105                 110

Ala Leu Gly Gly Leu Leu Gly Asn Val Phe Leu His Leu Leu Pro Glu
        115                 120                 125

Ala Trp Ala Tyr Thr Cys Ser Ala Ser Pro Gly Gly Glu Gly Gln Ser
    130                 135                 140

Leu Gln Gln Gln Gln Leu Gly Leu Trp Val Ile Ala Gly Ile Leu
145                 150                 155                 160

Thr Phe Leu Ala Leu Glu Lys Met Phe Leu Asp Ser Lys Glu Glu Gly
                165                 170                 175

Thr Ser Gln Ala Pro Asn Lys Asp Pro Thr Ala Ala Ala Ala Leu
            180                 185                 190

Asn Gly Gly His Cys Leu Ala Gln Pro Ala Ala Glu Pro Gly Leu Gly
        195                 200                 205

Ala Val Val Arg Ser Ile Lys Val Ser Gly Tyr Leu Asn Leu Leu Ala
    210                 215                 220

Asn Thr Ile Asp Asn Phe Thr His Gly Leu Ala Val Ala Ala Ser Phe
225                 230                 235                 240

Leu Val Ser Lys Lys Ile Gly Leu Leu Thr Thr Met Ala Ile Leu Leu
                245                 250                 255

His Glu Ile Pro His Glu Val Gly Asp Phe Ala Ile Leu Leu Arg Ala
            260                 265                 270

Gly Phe Asp Arg Trp Ser Ala Ala Lys Leu Gln Leu Ser Thr Ala Leu
        275                 280                 285

Gly Gly Leu Leu Gly Ala Gly Phe Ala Ile Cys Thr Gln Ser Pro Lys
    290                 295                 300

Gly Val Val Gly Cys Ser Pro Ala Ala Glu Thr Ala Ala Trp Val
305                 310                 315                 320

Leu Pro Phe Thr Ser Gly Gly Phe Leu Tyr Ile Ala Leu Val Asn Val
                325                 330                 335

Leu Pro Asp Leu Leu Glu Glu Glu Asp Pro Trp Arg Ser Leu Gln Gln
            340                 345                 350
```

Leu Leu Leu Leu Cys Ala Gly Ile Val Val Met Val Leu Phe Ser Leu
        355                 360                 365

Phe Val Asp
    370

<210> SEQ ID NO 9
<211> LENGTH: 2531
<212> TYPE: DNA
<213> ORGANISM: Homo sapiens

<400> SEQUENCE: 9

```
cagctaccat ggcccaaggg ctagaagtgg ccctcacaga cctccagagc tccagaaata    60
atgtgcggca ccacacggag gagatcactg tggaccacct gcttgttcgc cggggccagg   120
ccttcaacct caccctgtac ttcaggaacc ggagcttcca gccaggcctg acaacatca    180
tcttcgtggt tgaaactgag gatgctgtct acttggacag tgaacccag aggcaggagt    240
atgtcatgaa tgattatggc ttcatctacc aaggcagcaa gaactggatc cgcccatgtc   300
cctggaacta tggacagttt gaagacaaaa tcatagacat ctgcctgaag ctgctagaca   360
agagcctgca cttccagact gacccagcca cagactgtgc tctgcgggga agccccgtct   420
acgtcagcag agtggtgtgt gccatgatca acagcaatga tgataatggg gtgctcaatg   480
gaaactggag tgagaattac acagacggcg ccaaccctgc ggagtggacg ggcagcgtgg   540
ccatcctgaa gcagtggaac gccacaggct gccagcccgt gcgctacggg caatgctggg   600
tctttgctgc cgtcatgtgc acagtgatga ggtgtctggg gatccctacc cgtgtgatca   660
ccaacttcga ctctggccac gatacagatg gaaacctgat catagatgag tattatgaca   720
acacaggcag gattttgggg aataagaaga aggatactat ctggaacttc catgtctgga   780
atgagtgctg gatggcccgg aaggatctgc cccctgcata tggaggctgg caggtgctgg   840
acgccacacc tcaggagatg agcaacggcg tctactgctg tggccctgcc tctgtcagag   900
ccatcaaaga aggagaagtg gacctgaact atgacacgcc ctttgtgttt cgatggtga   960
atgctgactg catgtcctgg ctcgtccagg gagggaagga gcagaagctt caccaggaca  1020
cgagttctgt tggcaatttt atcagcacaa agagcatcca gagtgacgag cgggatgaca  1080
tcacagagaa ctacaagtat gaagaaggat ccctccagga gaggcaggtg tttctgaagg  1140
ctctgcagaa gctgaaggct agaagcttcc atggctccca agaggagca gagttgcaac  1200
cttccaggcc cacatcactg agccaggaca gccctcggag cctgcataca ccttcccttc  1260
gacccagtga tgtggtgcaa gtctccctga aattcaagct gctcgacccg cccaacatgg  1320
gccaggatat atgctttgtc ctgctggccc tcaacatgtc ctcccagttc aaggacctca  1380
aagtgaacct gagtgcccag tctctgctgc acgatgcag cccctgtcc ccattctggc  1440
aggacacagc gttcatcaca ctctctccta agaagcaaa gacctacccc tgcaaaatct  1500
cctattccca gtacagccag tacctgtcaa cagacaagct gatccgcatc agtgccctgg  1560
gtgaagagaa aagcagtcct gagaaaatcc tggtgaacaa gatcatcacc ttatcttatc  1620
caagcatcac gattaatgtt ctaggagcag ccgttgtgaa ccagccactc tccatacagg  1680
tgatattttc aaaccccctc tcggagcagg ttgaggactg tgtgctgact gtggaaggaa  1740
gtggcctctt caagaaacag cagaaagtct tccttggagt cctcaaaccc caacaccaag  1800
caagcatcat tctggagacc gtccccttca gagtggacaa aggcagatc caagctaata  1860
tgagaagcaa caagtttaag gacattaagg gttacaggaa tgtttatgta gactttgcat  1920
```

```
tataaattct ggaacaacgc gccagacgtg tgaatttcaa gcttcaggaa aaggagcaag   1980
ttcaaatgca agctgcgcca ttccccacca caacagaggc ttcacagggc tccagcaaga   2040
gccacagagg ggatgacgtg ttcatttcct gtctctcctg actccactag aaatttaagc   2100
tccatgaggg caaagacttt gctttgttta ctaccccctat actcagaacc atttctggca   2160
tatgctaggc actcaacaaa tatttttga atgaatgaat aggagactcc agcatccaga   2220
gaacaggtag gaaatgtcta tggatggata tttccctgga ccatttgcac agctcccctg   2280
gactcttttc agggcccagg gattccactg tgtcccatcc agagattcca ggattccagt   2340
ctcctatcca gaagcgtgat ttggcacaga ggtcagagga tactggtagg acttggccat   2400
gacttaactg ccccctgccc cagatatcca ggaaagaaaa agacaggctg aacagctcac   2460
tgttgttttg ttgttgcgaa agctaattcc ctagtatgaa taaacttcag accttgctct   2520
caaaaaaaaa a                                                        2531

<210> SEQ ID NO 10
<211> LENGTH: 638
<212> TYPE: PRT
<213> ORGANISM: Homo sapiens

<400> SEQUENCE: 10

Met Ala Gln Gly Leu Glu Val Ala Leu Thr Asp Leu Gln Ser Ser Arg
 1               5                  10                  15

Asn Asn Val Arg His His Thr Glu Ile Thr Val Asp His Leu Leu
                20                  25                  30

Val Arg Arg Gly Gln Ala Phe Asn Leu Thr Leu Tyr Phe Arg Asn Arg
            35                  40                  45

Ser Phe Gln Pro Gly Leu Asp Asn Ile Ile Phe Val Glu Thr Glu
    50                  55                  60

Asp Ala Val Tyr Leu Asp Ser Glu Pro Gln Arg Gln Glu Tyr Val Met
65                  70                  75                  80

Asn Asp Tyr Gly Phe Ile Tyr Gln Gly Ser Lys Asn Trp Ile Arg Pro
                85                  90                  95

Cys Pro Trp Asn Tyr Gly Gln Phe Glu Asp Lys Ile Ile Asp Ile Cys
            100                 105                 110

Leu Lys Leu Leu Asp Lys Ser Leu His Phe Gln Thr Asp Pro Ala Thr
        115                 120                 125

Asp Cys Ala Leu Arg Gly Ser Pro Val Tyr Val Ser Arg Val Val Cys
    130                 135                 140

Ala Met Ile Asn Ser Asn Asp Asp Asn Gly Val Leu Asn Gly Asn Trp
145                 150                 155                 160

Ser Glu Asn Tyr Thr Asp Gly Ala Asn Pro Ala Glu Trp Thr Gly Ser
                165                 170                 175

Val Ala Ile Leu Lys Gln Trp Asn Ala Thr Gly Cys Gln Pro Val Arg
            180                 185                 190

Tyr Gly Gln Cys Trp Val Phe Ala Ala Val Met Cys Thr Val Met Arg
        195                 200                 205

Cys Leu Gly Ile Pro Thr Arg Val Ile Thr Asn Phe Asp Ser Gly His
    210                 215                 220

Asp Thr Asp Gly Asn Leu Ile Ile Asp Glu Tyr Tyr Asp Asn Thr Gly
225                 230                 235                 240

Arg Ile Leu Gly Asn Lys Lys Lys Asp Thr Ile Trp Asn Phe His Val
                245                 250                 255

Trp Asn Glu Cys Trp Met Ala Arg Lys Asp Leu Pro Pro Ala Tyr Gly
```

```
            260                 265                 270
Gly Trp Gln Val Leu Asp Ala Thr Pro Gln Glu Met Ser Asn Gly Val
        275                 280                 285

Tyr Cys Cys Gly Pro Ala Ser Val Arg Ala Ile Lys Glu Gly Glu Val
        290                 295                 300

Asp Leu Asn Tyr Asp Thr Pro Phe Val Phe Ser Met Val Asn Ala Asp
305                 310                 315                 320

Cys Met Ser Trp Leu Val Gln Gly Gly Lys Glu Gln Lys Leu His Gln
                325                 330                 335

Asp Thr Ser Ser Val Gly Asn Phe Ile Ser Thr Lys Ser Ile Gln Ser
                340                 345                 350

Asp Glu Arg Asp Asp Ile Thr Glu Asn Tyr Lys Tyr Glu Glu Gly Ser
            355                 360                 365

Leu Gln Glu Arg Gln Val Phe Leu Lys Ala Leu Gln Lys Leu Lys Ala
        370                 375                 380

Arg Ser Phe His Gly Ser Gln Arg Gly Ala Glu Leu Gln Pro Ser Arg
385                 390                 395                 400

Pro Thr Ser Leu Ser Gln Asp Ser Pro Arg Ser Leu His Thr Pro Ser
                405                 410                 415

Leu Arg Pro Ser Asp Val Val Gln Val Ser Leu Lys Phe Lys Leu Leu
                420                 425                 430

Asp Pro Pro Asn Met Gly Gln Asp Ile Cys Phe Val Leu Leu Ala Leu
            435                 440                 445

Asn Met Ser Ser Gln Phe Lys Asp Leu Lys Val Asn Leu Ser Ala Gln
450                 455                 460

Ser Leu Leu His Asp Gly Ser Pro Leu Ser Pro Phe Trp Gln Asp Thr
465                 470                 475                 480

Ala Phe Ile Thr Leu Ser Pro Lys Glu Ala Lys Thr Tyr Pro Cys Lys
                485                 490                 495

Ile Ser Tyr Ser Gln Tyr Ser Gln Tyr Leu Ser Thr Asp Lys Leu Ile
                500                 505                 510

Arg Ile Ser Ala Leu Gly Glu Glu Lys Ser Ser Pro Glu Lys Ile Leu
            515                 520                 525

Val Asn Lys Ile Ile Thr Leu Ser Tyr Pro Ser Ile Thr Ile Asn Val
530                 535                 540

Leu Gly Ala Ala Val Val Asn Gln Pro Leu Ser Ile Gln Val Ile Phe
545                 550                 555                 560

Ser Asn Pro Leu Ser Glu Gln Val Glu Asp Cys Val Leu Thr Val Glu
                565                 570                 575

Gly Ser Gly Leu Phe Lys Lys Gln Gln Lys Val Phe Leu Gly Val Leu
                580                 585                 590

Lys Pro Gln His Gln Ala Ser Ile Ile Leu Glu Thr Val Pro Phe Lys
            595                 600                 605

Ser Gly Gln Arg Gln Ile Gln Ala Asn Met Arg Ser Asn Lys Phe Lys
610                 615                 620

Asp Ile Lys Gly Tyr Arg Asn Val Tyr Val Asp Phe Ala Leu
625                 630                 635

<210> SEQ ID NO 11
<211> LENGTH: 21
<212> TYPE: DNA
<213> ORGANISM: Artificial Sequence
<220> FEATURE:
<223> OTHER INFORMATION: Synthetic primer
```

<400> SEQUENCE: 11
agaccccttt tgattcagac a                                                21

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12 aaggttttc ggtaattttt aagg                                              24

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
ctcaatggag gccactgtct                                                  20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14 atggggatg agagccttag                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
tcccagggaa gctcataaaa                                                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
gccgataaaa cctccaacct                                                  20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
tatgtgccca acaacagagg                                                  20

<210> SEQ ID NO 18
<211> LENGTH: 20

```
<212> TYPE: DNA
<213> ORGANISM: Artificial Sequence
<220> FEATURE:
<223> OTHER INFORMATION: Synthetic primer

<400> SEQUENCE: 18
gccagagagt tgggagagaa                                              20

<210> SEQ ID NO 19
<211> LENGTH: 24
<212> TYPE: DNA
<213> ORGANISM: Artificial Sequence
<220> FEATURE:
<223> OTHER INFORMATION: Synthetic primer

<400> SEQUENCE: 19
tctgtttaag caaagatgat ttgg                                         24

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
agggcctcag ctctacttcc                                              20
```

US 9,714,450 B2

METHODS FOR DIAGNOSING AND TREATING SCHIZOPHRENIA

CROSS REFERENCE TO RELATED APPLICATION

This application claims priority under 35 USC §119(e) from U.S. Provisional Application Ser. No. 61/695,597, filed Aug. 31, 2012, which application is herein specifically incorporated by reference in its entirety.

GOVERNMENT RIGHTS

The research leading to the present invention was funded in part by grant number R01MH059114 from the National Institute of Health. The United States government has certain rights in the invention.

FIELD OF THE INVENTION

Genetic markers of schizophrenia (SCZ) are presented herein. Methods for using such genetic markers for assessing risk of developing SCZ and diagnosing SCZ are also encompassed herein. Identification of subjects having these genetic markers is also instructive with respect to predicting and/or determining efficacy of a therapeutic regimen in a subject having these markers. A determination of a subject's status with regard to these genetic markers also provides guidance with respect to choosing a regimen for treating the subject.

BACKGROUND OF THE INVENTION

Several publications and patent documents are referenced in this application in order to more fully describe the state of the art to which this invention pertains. The disclosure of each of these publications and documents is incorporated by reference herein in its entirety.

SCZ is a severe neuropsychiatric illness with onset in late adolescence or early adulthood. Typified by distorted perceptions of reality (hallucinations and delusions), social deficits, disorganized language and behavior, and mild cognitive dysfunction, it is a devastating and relatively common disorder, affecting about 1% of worldwide populations. The prevailing theory is that SCZ results from anomalous neurodevelopment, either from a teratogenic fetal exposure or from defective genes. Cores of family, twin, and adoption studies have confirmed a major hereditary component for SCZ risk, yet no particular gene has been identified for the disorder. The present consensus is that SCZ is an etiologically heterogeneous syndrome, with multiple genes, various exposures, and gene-environment interactions producing a common phenotype. For many genetic diseases, the birth of an affected individual into an otherwise unaffected family (sporadic case) signals a possible de novo mutation. In contrast, sporadic cases of SCZ are usually presumed to originate from environmental factors that either act independently or through synergistic effects with underlying genes. See, e.g., Malaspina et al. (Am J Med Genetics (Neuropsychiatric Genetics) 2002, 114:299-303).

SUMMARY

A method for treating a mammalian subject (e.g., a human) having or suspected of having schizophrenia is presented herein, the method comprising: selecting a mammalian subject that has been determined to have a haplotype comprising a mutated Bruton's tyrosine kinase (BTK) gene, wherein the mutated BTK gene encodes a BTK protein having enhanced kinase activity, and treating the mammalian subject with the haplotype comprising the mutated BTK gene with a BTK inhibitor. In a particular aspect thereof, the BTK protein having enhanced kinase activity comprises at least one amino acid that is altered relative to wildtype BTK protein. In a more particular aspect, the mutated BTK gene comprises a mutation in the codon encoding amino acid position 255 of the BTK protein. In an even more particular aspect, the mutation replaces arginine at amino acid position 255 with glutamine in the BTK protein. In a further aspect, the BTK inhibitor is PCI-32765, PCI-33380, PCI-29732, AVL-292, or ONO-WG-307. The method may further comprise determining the haplotype of the mammalian subject with respect to an assessment of the presence of at least one of a mutated kinase-associated phosphatase, cell cycle control protein (CDKN3/KAP) gene; a mutated protein tyrosine phosphatase receptor (PTPRG) gene; a mutated zinc transporter (SLC39A13) gene; or a mutated transglutaminase 5 (TGM5) gene.

In a particular embodiment thereof, the mammalian subject is a mouse, rat, or a primate, and more particularly, a human. In addition to mammalian subjects, methods described herein also relate to insects and, in particular, to Drosophila species and cells derived therefrom.

Also encompassed herein is a method for diagnosing a mammalian subject (e.g., a human) with schizophrenia comprising determining if the mammalian subject has a haplotype comprising a mutated Bruton's tyrosine kinase (BTK) gene, wherein the mutated BTK gene comprises a mutation in the codon encoding amino acid position 255 of the BTK protein whereby arginine at amino acid position 255 of wildtype BTK protein is replaced with a different amino acid, and wherein identification of the haplotype comprising the mutated BTK gene diagnoses the mammalian subject as having schizophrenia. In an embodiment thereof, the mutation replaces arginine at amino acid position 255 with glutamine in the BTK protein.

Also encompassed herein is a method for diagnosing a mammalian subject (e.g., a human) with schizophrenia comprising determining if the mammalian subject has a haplotype comprising a mutated Kinase-associated phosphatase, cell cycle control protein (CDKN3/KAP) gene, wherein the mutated CDKN3/KAP gene comprises a mutation in the codon encoding amino acid position 79 of the CDKN3/KAP protein whereby cysteine at amino acid position 79 of wildtype CDKN3/KAP protein is replaced with a different amino acid and wherein identification of the haplotype comprising the mutated CDKN3/KAP gene diagnoses the mammalian subject as having schizophrenia. In an embodiment thereof, the mutation replaces cysteine at amino acid position 79 with phenylalanine in the CDKN3/KAP protein.

Also encompassed herein is a method for diagnosing a mammalian subject (e.g., a human) with schizophrenia comprising determining if the mammalian subject has a haplotype comprising a mutated Protein tyrosine phosphatase receptor (PTPRG) gene, wherein the mutated PTPRG gene comprises a mutation in the codon encoding amino acid position 422 of the PTPRG protein whereby the mutation introduces a stop codon at amino acid position 422 and wherein identification of the haplotype comprising the mutated PTPRG gene diagnoses the mammalian subject as having schizophrenia.

Also encompassed herein is a method for diagnosing a mammalian subject (e.g., a human) with schizophrenia comprising determining if the mammalian subject has a haplotype comprising a mutated solute carrier transporter family 39A13 (SLC39A13) gene, wherein the mutated SLC39A13 gene comprises a mutation in the codon encoding amino acid position 228 of the SLC39A13 protein whereby aspartic acid at amino acid position 228 of wildtype SLC39A13 protein is replaced with a different amino acid and wherein identification of the haplotype comprising the mutated SLC39A13 gene diagnoses the mammalian subject as having schizophrenia. In an embodiment thereof, the mutation replaces aspartic acid at amino acid position 228 with asparagine in the SLC39A13 protein.

Also encompassed herein is a method for diagnosing a mammalian subject (e.g., a human) with schizophrenia comprising determining if the mammalian subject has a haplotype comprising a mutated transglutaminase 5 (TGM5) gene, wherein the mutated TGM5 gene comprises a mutation in the codon encoding amino acid position 139 of the TGM5 protein whereby leucine at amino acid position 139 of wildtype TGM5 protein is replaced with a different amino acid and wherein identification of the haplotype comprising the mutated TGM5 gene diagnoses the mammalian subject as having schizophrenia. In an embodiment thereof, the mutation replaces leucine at amino acid position 139 with isoleucine in the TGM5 protein.

In an aspect of above methods, the mammalian subject (e.g., a human) exhibits symptoms indicative of schizophrenia. Accordingly, the present methods may be performed in conjunction with other approaches dedicated to diagnosing schizophrenia in a subject. In a further aspect thereof, the mammalian subject is "cancer-free".

In accordance with the findings presented herein, determining the haplotype of a subject is achieved by analyzing a sample isolated from the human subject. As exemplified herein, such a sample can be, without limitation, blood, plasma, lymph, buccal cells, or a tissue biopsy.

In a further aspect, determining the haplotype of a subject is achieved by performing by nucleic acid sequencing. For example, an initial PCR product that flanks the mutation in question can be generated, which is then sequenced.

Also encompassed herein is a method for diagnosing a mammalian subject (e.g., a human) with schizophrenia comprising determining if the mammalian subject has a haplotype comprising at least two of: a mutated Bruton's tyrosine kinase (BTK) gene, wherein the mutated BTK gene comprises a mutation in the codon encoding amino acid position 255 of the BTK protein whereby arginine at amino acid position 255 of wildtype BTK protein is replaced with a different amino acid; a mutated Kinase-associated phosphatase, cell cycle control protein (CDKN3/KAP) gene, wherein the mutated CDKN3/KAP gene comprises a mutation in the codon encoding amino acid position 79 of the CDKN3/KAP protein whereby cysteine at amino acid position 79 of wildtype CDKN3/KAP protein is replaced with a different amino acid; a mutated Protein tyrosine phosphatase receptor (PTPRG) gene, wherein the mutated PTPRG gene comprises a mutation in the codon encoding amino acid position 422 of the PTPRG protein whereby the mutation introduces a stop codon at amino acid position 422; a mutated solute carrier transporter family 39A13 (SLC39A13) gene, wherein the mutated SLC39A13 gene comprises a mutation in the codon encoding amino acid position 228 of the SLC39A13 protein whereby aspartic acid at amino acid position 228 of wildtype SLC39A13 protein is replaced with a different amino acid; and a mutated transglutaminase 5 (TGM5) gene, wherein the mutated TGM5 gene comprises a mutation in the codon encoding amino acid position 139 of the TGM5 protein whereby leucine at amino acid position 139 of wildtype TGM5 protein is replaced with a different amino acid; and wherein identification of at least two of the haplotypes diagnoses the mammalian subject as having schizophrenia. In further aspects thereof, identification of at least three, or at least four, or all five of the haplotypes diagnoses the mammalian subject as having schizophrenia.

In more particular embodiments thereof, the BTK mutation replaces arginine at amino acid position 255 with glutamine in the BTK protein; the CDKN3/KAP mutation replaces cysteine at amino acid position 79 with phenylalanine in the CDKN3/KAP protein; the SLC39A13 mutation replaces aspartic acid at amino acid position 228 with asparagine in the SLC39A13 protein; and/or the TGM5 mutation replaces leucine at amino acid position 139 with isoleucine in the TGM5 protein.

In a further aspect of the above method, the mammalian subject (e.g., a human) exhibits symptoms indicative of schizophrenia. Accordingly, the present methods may be performed in conjunction with other approaches dedicated to diagnosing schizophrenia in a subject. In a further aspect thereof, the mammalian subject is determined to be "cancer-free".

In accordance with findings presented herein, determining the haplotype of a subject is achieved by analyzing a sample isolated from the mammalian subject (e.g., a human). As exemplified herein, such a sample can be, without limitation, blood, plasma, lymph, buccal cells, or a tissue biopsy. In a further aspect, determining the haplotype of a subject is achieved by performing by nucleic acid sequencing.

Also encompassed herein are cDNA molecules encoding a mutated BTK protein comprising glutamine at amino acid position 255, rather than the wildtype residue arginine; a mutated CDKN3/KAP protein comprising phenylalanine at amino acid position 79, rather than the wildtype residue cysteine; a mutated SLC39A13 protein comprising asparagine at amino acid position 228, rather than the wildtype residue aspartic acid; a mutated PTPRG protein truncated at amino acid position 422; and/or a mutated TGM5 protein comprising isoleucine at amino acid position 139, rather than the wildtype residue leucine. In a particular embodiment thereof, the cDNA molecule encoding the mutated BTK protein comprises a point mutation corresponding to ChrX: 100.615.568, whereby a thymidine (T) replaces a cytosine (C); the cDNA molecule encoding the mutated CDKN3/KAP protein comprises a point mutation corresponding to Chr14: 54.878.244, whereby an adenine (A) replaces a guanine (G); the cDNA molecule encoding the mutated SLC39A13 protein comprises a point mutation corresponding to Chr11: 47.435.184, whereby an adenine (A) replaces a guanine (G); the cDNA molecule encoding the mutated PTPRG protein comprises a point mutation corresponding to Chr3: 62.180.781, whereby a thymidine (T) replaces a cytosine (C); and the cDNA molecule encoding the mutated TGM5 protein comprises a point mutation corresponding to Chr15: 44.552.271, whereby a thymidine (T) replaces a guanine (G). Also encompassed herein are vectors comprising such cDNA molecules and cells comprising such vectors, which can be used to express large quantities of the aforementioned mutated proteins.

BRIEF DESCRIPTION OF THE DRAWINGS

FIG. 3 depicts a schematic of the Protein tyrosine phosphatase receptor (PTPRG) gene and a point mutation identified therein that is associated with SCZ.

DETAILED DESCRIPTION OF THE INVENTION

Methods for assessing genetic risk for developing SCZ based on an evaluation of single nucleotide variations (SNVs) are described herein. Evidence is presented that supports an association of the disclosed SNVs and genotypes with SCZ. Specific allelic and genotypic variants identified herein can be used to assess genetic risk for SCZ and render a diagnosis of SCZ. A genetic diagnosis of SCZ by identification of one of more of the de novo mutations identified herein can, moreover, provide guidance as to what therapeutic intervention would confer greatest benefit to a subject in need thereof. Accordingly, methods and compositions for treating SCZ based on the haplotype status are encompassed herein.

Figure 1:
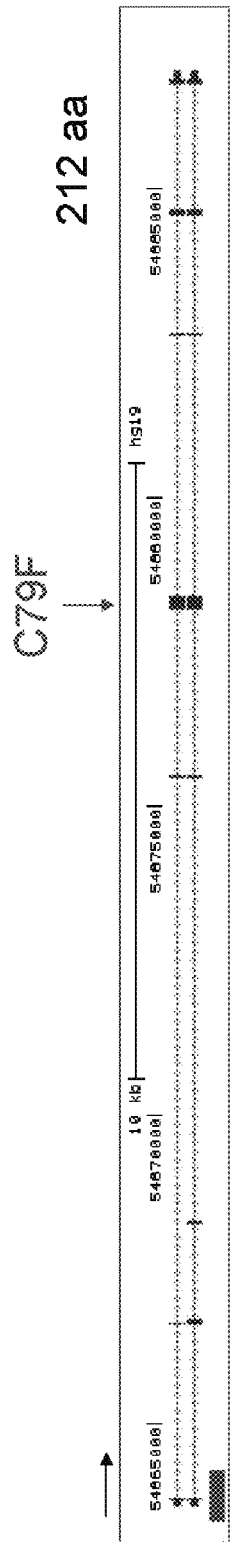
FIG. 1 depicts a schematic of the Kinase-associated phosphatase, cell cycle control protein (CDKN3/KAP) gene and a point mutation identified therein that is associated with SCZ.
Figure 2:
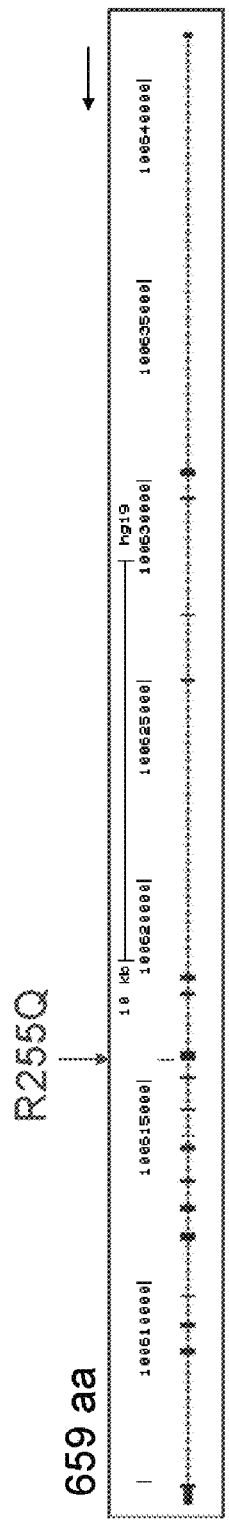
FIG. 2 depicts a schematic of the Bruton's tyrosine kinase (BTK) gene and a point mutation identified therein that is associated with SCZ.
Figure 4:
FIG. 4 depicts a schematic of the Zinc transporter (SLC39A13) gene and a point mutation identified therein that is associated with SCZ.
Figure 5:
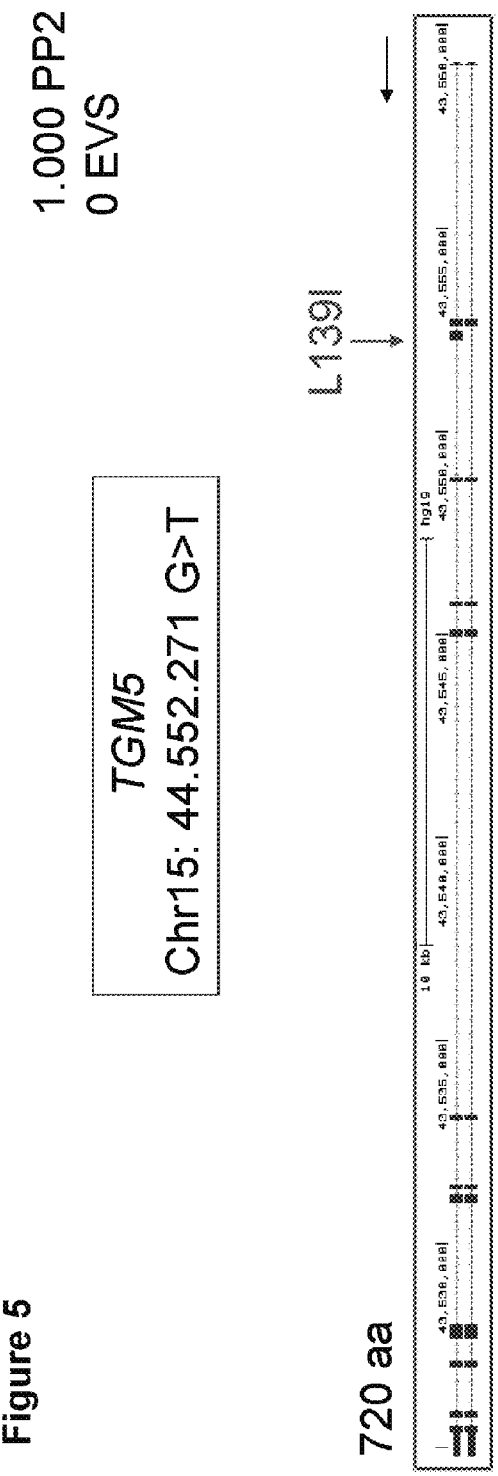
FIG. 5 depicts a schematic of the transglutaminase 5 (TGM5) gene and a point mutation identified therein that is associated with SCZ.

As described herein, the present inventors have identified five validated de novo mutations in five different genes. The five different genes in which point mutations have been identified and whose presence correlates positively with or is associated with SCZ are: Kinase-associated phosphatase, cell cycle control protein (CDKN3/KAP); Bruton's tyrosine kinase (BTK); Protein tyrosine phosphatase receptor (PTPRG); Zinc transporter (SLC39A13); and transglutaminase 5 (TGM5). See, for example, FIGS. 1-5.

CDKN3/KAP is found on chromosome 14 and the location therein of the point mutation whereby a guanine (G) is altered to become an adenine (A) is Chr14: 54.878.244. See also FIG. 1. CDKN3/KAP is a 212 amino acid long protein which belongs to the dual specificity protein phosphatase family. It was identified as a cyclin-dependent kinase inhibitor, and has been shown to interact with and dephosphorylate CDK2 kinase, thus preventing activation of CDK2 kinase. The gene has been reported to be deleted, mutated, or overexpressed in several kinds of cancers.

The mutation identified herein results in the presence of phenylalanine (F) rather than cysteine (C) at amino acid position 79 of CDKN3/KAP (C79F). The polyphen designation of 1.000 indicates that it is likely that the mutation increases phosphatase activity. Intriguingly, maternal dietary choline deficiency reduces DNA methylation of CDKN3 in developing hippocampus of mouse fetal brain.

BTK is found on the X chromosome and the location therein of the point mutation whereby a cytosine (C) is altered to become a thymidine (T) is ChrX: 100.615.568. See also FIG. 2. BTK is a 659 amino acid long protein that includes a tyrosine kinase domain and a pleckstrin homology (PH) domain. Upon PH domain-mediated binding to phosphatidylinositol (3,4,5)-trisphosphate (PIP3), BTK phosphorylates phospholipase C, which in turn hydrolyzes PIP2, a phosphatidylinositol, into two second messengers, inositol triphosphate (IP3) and diacylglycerol (DAG), which then go on to modulate the activity of downstream proteins during, for example, B-cell signalling. The mutation identified therein results in the presence of glutamine (Q) rather than arginine (R) at amino acid position 255 of BTK (R255Q). The polyphen designation of 0.994 indicates that it is likely that the mutation increases kinase activity. BTK is critical to B-cell development and is also involved in immunoregulation of dendritic cells. Activation of BTK is also important in neuronal differentiation of hippocampal progenitor cells.

PTPRG is found on chromosome 3 and the location therein of the point mutation whereby a cytosine (C) is altered to become a thymidine (T) is Chr3: 62.180.781. See also FIG. 3.

PTPRG is 1445 amino acids long and includes an extracellular region, a single transmembrane region, and two tandem intracytoplasmic catalytic domains. The extracellular region includes a carbonic anhydrase-like (CAH) domain. The PTPRG gene is located in a chromosomal region that is frequently deleted in renal cell carcinoma and lung carcinoma, and thus is thought to be a candidate tumor suppressor gene. PTPRG is expressed in the brain, wherein the highest expression levels have been detected in the hippocampus and sensory neurons. The mutation identified herein results in the presence of a stop codon rather than one encoding arginine (R) at amino acid position 422 of PTPRG (R422stop). The polyphen designation of 1.000 indicates that it is likely that the mutation increases phosphatase activity. Over-expression of PTPRG in neuronal cells prevents neurite outgrowth following treatment with NGF. It is also upregulated by cytokines in astrocytoma cells, suggesting that it may be involved in inflammatory diseases of the brain.

Further to the above, the present inventor views the mutated genes described herein as associated with de novo SCZ in the context of their roles relating to inflammation and the endothelium. Inflammation is, indeed, understood to play a potentially significant role in SCZ. This is underscored by growing evidence from clinical studies with COX-2 inhibitors indicating that anti-inflammatory agents have potential in the treatment of SCZ, particularly in the early stages of disease. See, for example, Muller et al. 2012, Advances in Protein Chemistry and Structural Biology 88:49-68. The role of inflammation in SCZ is discussed in greater detail herein below.

SLC39A13 is found on chromosome 11 and the location therein of the point mutation whereby a guanine (G) is altered to become an adenine (A) is Chr11: 47.435.184. See also FIG. 4.

SLC39A13 is a 321 amino acid long protein that has been identified as a zinc transporter that comprises eight transmembrane domains. The mutation identified therein results in the presence of asparagine (N) rather than aspartic acid (D) at amino acid position 228 of SLC39A13 (D228N). The polyphen designation of 1.000 indicates that it is likely that the mutation increases transporter activity. It is expressed at highest levels in ganglia and connective tissue.

TGM5 is found on chromosome 15 and the location therein of the point mutation whereby a guanine (G) is altered to become a thymidine (T) is Chr15: 44.552.271. See also FIG. 5.

TGM5 is a 720 amino acid long protein that has been identified as a transglutaminase that stabilizes protein structures. The mutation identified therein results in the presence of isoleucine (I) rather than leucine (L) at amino acid position 139 of TGM5 (L139I). The polyphen designation of 1.000 indicates that it is likely that the mutation increases transglutaminase activity. It is ubiquitously expressed and functions in the differentiation of epidermal tissues. Recessive mutations in TGM5 are associated with acral peeling skin syndrome. See, for example, Pigors et al. J Invest Dermatol 2012, 132:2422-9, the entire content of which is incorporated herein in its entirety.

PolyPhen-2 (PP2) is an automatic tool for prediction of possible impact of an amino acid substitution on the structure and function of a human protein. This prediction is based on a number of features comprising the sequence, phylogenetic and structural information characterizing the substitution. For a given amino acid substitution in a protein, PP2 extracts various sequence and structure-based features of the substitution site and feeds them to a probabilistic classifier. Accordingly, PP2 predicts the functional significance of an allele replacement from its individual features by Naïve Bayes classifier trained using supervised machine-learning.

Thus, in accordance with the identification of point mutations in CDKN3/KAP, BTK, PTPRG, SLC39A13, and/or TGM5 genes, the presence of which correlates positively with or is associated with SCZ, methods are presented herein to identify subjects with a predisposition for developing SCZ or to diagnose subjects with SCZ. Further to the above, identifying subjects with a predisposition for developing SCZ or diagnosis of a subject as having SCZ would be accompanied and complemented by an assessment of symptoms in the subject that are known to be associated with neuropsychiatric illnesses. Such symptoms are known in the art and routinely used in diagnoses of SCZ-spectrum disorders, Schizotypal Personality Disorder (SPD) and Schizoaffective Disorder (SD), as well as SCZ and affective psychotic disorders. Such symptoms include: distorted perceptions of reality (hallucinations and delusions), social deficits, disorganized language and behavior, and mild cognitive dysfunction.

The identification of point mutations in CDKN3/KAP, BTK, PTPRG, SLC39A13, and TGM5 genes that correlate positively with or are associated with SCZ can also be used to advantage in the identification of subjects who would benefit from a particular therapeutic regimen directed to addressing the altered activity of the protein encoded by one or another of the genes comprising an SNV identified herein. The identification of point mutations in CDKN3/KAP, BTK, PTPRG, SLC39A13, and TGM5 genes that correlate positively with or are associated with SCZ is also useful with regard to stratification of subjects in a population thereof to identify which subjects would benefit from a particular therapeutic regimen directed to addressing the altered activity of the protein encoded by one or another of the genes comprising an SNV identified herein. Such a pharmacogenomic approach is based on the concept that the identification of an SNV in a protein confers altered activity to the mutated protein comprising the SNV and the signaling pathway or pathways in which the protein functions in a cell and thus, administration of a therapeutic agent to at least partially restore normal wildtype activity for the mutated protein would provide a targeted approach toward re-establishing a wildtype phenotype in the cell. Such a targeted therapeutic approach would also restore normal activity to the signaling pathways in which the mutated protein functions.

An exemplary pharmacogenomic approach is suggested by the identification of an SNV in the BTK gene, which is predicted to encode a BTK protein with enhanced kinase activity. Accordingly, these findings suggest that administration of a therapeutically effective amount of a BTK specific tyrosine kinase activity inhibitor would confer benefit to a patient identified with a variant BTK haplotype such as that described herein. See, for example, FIG. 2. PCI-32765, an oral inhibitor of BTK, is set forth herein as an exemplary therapeutic agent for the treatment of patients exhibiting symptoms of SCZ who are identified as having the variant BTK haplotype. PCI-32765 has been shown to be effective in the treatment of chronic lymphocytic leukemia and mantle cell lymphoma, respectively.

More particularly, small trials with PCI-32765 (a first-in-class compound) have demonstrated substantial efficacy with low toxicity in poor-prognosis chronic lymphocytic leukemia and mantle cell lymphoma. About 90% of patients with CLL exhibited clinical responses to PCI-32765, which was administered once a day orally, in a phase I/II study. About two-thirds of the patients with previously treated mantle cell lymphoma exhibited complete or partial responses to PCI-32765 in preliminary data from an ongoing phase II trial. Both studies revealed that treatment with PCI-32765 led to rapid shrinkage of lymph nodes swollen with malignant cells, accompanied by large increases in lymphocyte counts in circulation. See Ponader et al. [Blood (ASH Annual Meeting Abstracts) 2011 118: Abstract 3688, the entire content of which is incorporated herein by reference].

In the study pertaining to CLL, preliminary data on 61 patients with relapsed or refractory CLL who received 420 or 840 mg/day of PCI-32765 was reported. The trial also included 56 other patients who were either treatment-naive or had high-risk previously treated disease. The trial protocol initially called only for the 420-mg/day dosage, but it was later amended to include the higher dose. Hence, median follow-up was 12.6 months for the 27 patients taking the lower dose and 9.3 months for 34 patients taking 840 mg/day. Most of the clinical responses were classified as partial according to standard criteria, which require at least 50% reduction in node volume and 50% reduction in lymphocyte counts. This standard was met by 63% of low-dose and 68% of high-dose patients. Another 23%, evenly divided between dosage groups, had "nodal" responses, wherein 50% or greater reductions in node volume were detected, but in the absence of a 50% decline in lymphocyte counts.

In the study pertaining to mantle cell lymphoma, results on 68 patients with previously treated mantle cell lymphoma receiving 560 mg/day of PCI-32765 were reported. Early on in the trial, objective responses (partial plus complete) were observed in 69% of 51 patients evaluable for efficacy. About 15% of patients exhibited complete responses. Scores on the MCL International Prognostic Index appear unrelated to response, since patients classified with low, intermediate, or high risk all showed response rates of 65% to 75%.

In a related report, Chen et al. have shown that PCI-32765 mobilizes tumor cells out of lymph nodes and other tissues and prevents them from reentering these tissues by blocking the action of BTK. The cells are, therefore, essentially exiled to the peripheral blood, where they eventually undergo apoptosis and die. See Chen et al. [Blood (ASH Annual Meeting Abstracts) 2011 118: Abstract 982].

Additional studies relating to administration of PCI-32765 to patients are described by, for example, Balasubramanian et al. [Blood (ASH Annual Meeting Abstracts) 2011 118: Abstract 4969].

The chemical structure of BTK inhibitors, including PCI-32765, is as follows:

PCI-32765

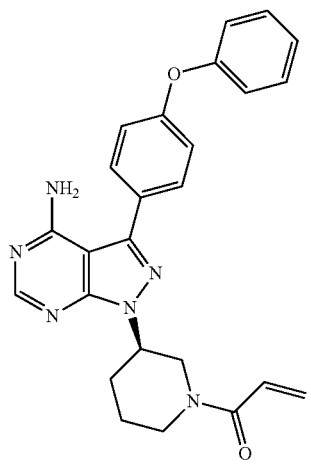

PCI-33380

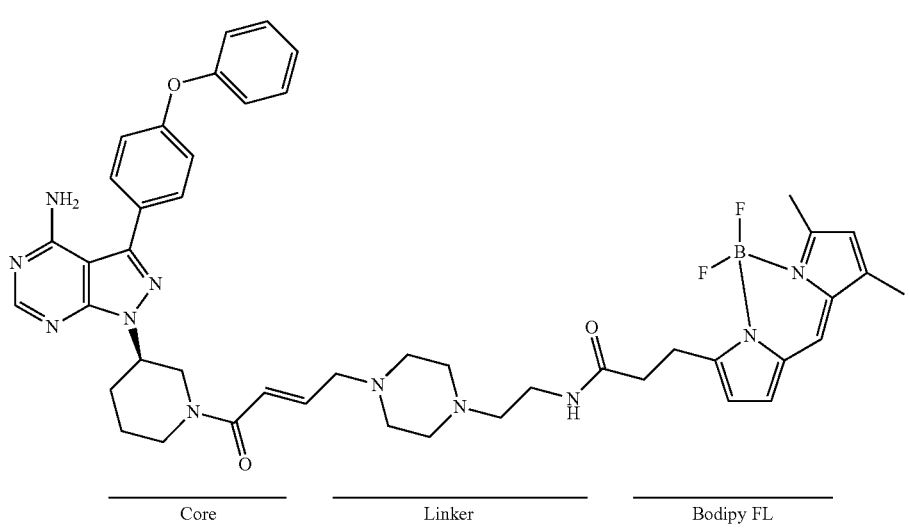

PCI-29732

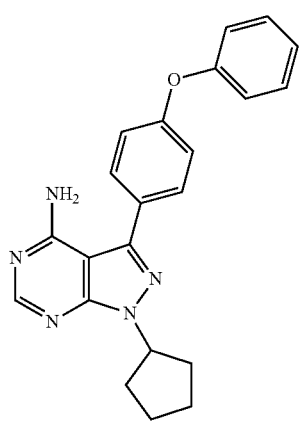

As described in Honigberg et al. (Proc Natl Acad Sci 2010; 107:13075-130800), PCI-32765 is an irreversible BTK inhibitor, PCI-33380 (which also serves as a probe by virtue of the Bodipy FL label) is an irreversible BTK inhibitor, and PCI-29732 is a reversible BTK inhibitor. The content of Honigberg et al. (Proc Natl Acad Sci 2010; 107:13075-130800) is incorporated herein by reference in its entirety.

Phase III trial designs for administration of PCI-32765 have been developed and such studies have a projected start date in 2012.

In keeping with these studies, it is envisioned that PCI-32765 can be administered to subjects exhibiting symptoms of SCZ who are identified as having the variant BTK haplotype described herein at 420, 560, or 840 mg/day. Based on these studies, a range of 300-900 mg/day is envisioned herein. Particular dosage range for treatment of such patients may, however, vary and may, indeed, be increased so as to ensure proper dosing to nervous tissue. In a particular embodiment, PCI-32765 is administered to a subject orally.

Other BTK inhibitors that are envisioned for the treatment of subjects exhibiting symptoms of SCZ who are identified as having the variant BTK haplotype described herein include, without limitation, AVL-292, as described by Evans et al. [Blood (ASH Annual Meeting Abstracts) 2011 118: Abstract 3485] and ONO-WG-307, as described by Kozaki et al. [Blood (ASH Annual Meeting Abstracts) 2011 118: Abstract 3731]. The structure of AVL-292 is presented in, for example, U.S. Pat. No. 7,982,036, the entire content of which is incorporated herein by reference.

Also encompassed herein is a method of identifying a subject at risk for schizophrenia, comprising: determining at least one of (a) BTK ChrX: 100.615.568 T/C genotype of the subject from a biological sample taken from the subject; determining the presence of a T allele at the BTK ChrX: 100.615.568 T/C genotype; and determining that the subject has an increased risk for schizophrenia based on the presence of the T allele at the BTK ChrX: 100.615.568 T/C genotype; (b) CDKN3/KAP Chr14: 54.878.244 A/G genotype of the subject from a biological sample taken from the subject; determining the presence of an A allele at the CDKN3/KAP Chr14: 54.878.244 A/G genotype; and determining that the subject has an increased risk for schizophrenia based on the presence of the A allele at the CDKN3/KAP Chr14: 54.878.244 A/G genotype; (c) SLC39A13 Chr11: 47.435.184 A/G genotype of the subject from a biological sample taken from the subject; determining the presence of an A allele at the SLC39A13 Chr11: 47.435.184 A/G genotype; and determining that the subject has an increased risk for schizophrenia based on the presence of the A allele at the SLC39A13 Chr11: 47.435.184 A/G genotype; (d) PTPRG Chr3: 62.180.781 T/C genotype of the subject from a biological sample taken from the subject; determining the presence of a T allele at the PTPRG Chr3: 62.180.781 T/C genotype; and determining that the subject has an increased risk for schizophrenia based on the presence of the T allele at the PTPRG Chr3: 62.180.781 T/C genotype; and (e) TGM5 Chr15: 44.552.271 T/G genotype of the subject from a biological sample taken from the subject; determining the presence of a T allele at the TGM5 Chr15: 44.552.271 T/G genotype; and determining that the subject has an increased risk for schizophrenia based on the presence of the T allele at the TGM5 Chr15: 44.552.271 T/G genotype, wherein determining that the subject has an increased risk for schizophrenia based on the presence of two, three, four, or all five of these schizophrenia-predisposing genotypes indicates that the subject is at greater risk for schizophrenia than if the presence of only one of these schizophrenia-predisposing genotypes is detected.

Also encompassed herein is a method for identifying an increased susceptibility to schizophrenia comprising detecting at least one of (a) a BTK ChrX: 100.615.568 T/C mutation in a BTK nucleic acid sequence in a sample from a mammalian subject, and identifying said subject as having an increased susceptibility to schizophrenia; (b) a CDKN3/KAP Chr14: 54.878.244 A/G mutation in a CDKN3/KAP nucleic acid sequence in a sample from a mammalian subject, and identifying said subject as having an increased susceptibility to schizophrenia; (c) a SLC39A13 Chr11: 47.435.184 A/G mutation in a SLC39A13 nucleic acid sequence in a sample from a mammalian subject, and identifying said subject as having an increased susceptibility to schizophrenia; (d) a PTPRG Chr3: 62.180.781 T/C mutation in a PTPRG nucleic acid sequence in a sample from a mammalian subject, and identifying said subject as having an increased susceptibility to schizophrenia; and (e) a TGM5 Chr15: 44.552.271 T/G mutation in a TGM5 nucleic acid sequence in a sample from a mammalian subject, and identifying said subject as having an increased susceptibility to schizophrenia; wherein identifying that the subject has an increased risk for schizophrenia based on the presence of two, three, four, or all five of these schizophrenia-predisposing mutations indicates that the subject is at greater risk for schizophrenia than if the presence of only one of these schizophrenia-predisposing mutations is identified.

BTK

BTK is a component of the B-cell antigen receptor signaling pathway. It was initially discovered in genetic studies of an inherited disorder called X-linked agammaglobulinemia, a disorder which is causally linked to defects in the BTK gene. Because downstream activity of the B-cell antigen receptor system is known to be involved in various hematologic cancers, BTK is the focus of intense drug development efforts. PCI-32765 has emerged as the most advanced of several investigational compounds targeting the enzyme. The NCBI Reference Sequences corresponding to human BTK are as follows: NM_000061, NC_000023.10, NC_018934.1, and NT_011651.17, the entire content of each of which is incorporated herein in its entirety.

Nucleic and amino acid sequences accessible via Accession No. NM_000061 [defined as *Homo sapiens* Bruton agammaglobulinemia tyrosine kinase (BTK), mRNA] are designated SEQ ID NO: 1 and 2, respectively.

Additional information pertaining to the human BTK gene can be accessed via the worldwide web site maintained by the University of California at Santa Cruz (UCSC) Genome Bioinformatics site [Reference No. Human BTK gene (uc004ehg.2)].

CDKN3/KAP

Cyclin-dependent kinase inhibitor 3 is a member of the dual specificity protein tyrosine phosphatase family. It was identified as a cyclin-dependent kinase inhibitor and has been shown to interact with and dephosphorylate CDK2 kinase, thereby preventing activation of CDK2 kinase. The CDKN3/KAP gene has been reported to be deleted, mutated, or overexpressed in several kinds of cancers. See, for example, Gyuris et al. 1993, Cell 75:791-803; Demetrick et al. 1995, Cytogenet Cell Genet 69:190-192; Yeh et al. 2003, Biochem Biophys Res Commun 305: 311-4; Hannon et al. 1994, Proc Natl Acad Sci 91:1731-1735; and Harper et al. 1993, Cell 75-805-816; and Donato et al. 2002, J Clin Invest 109:51-58. The NCBI Reference Sequences corresponding to human CDKN3/KAP include the following: NM_001130851, NC_000017.10, NC_018928.1, and NT_010783.15, the entire content of each of which is incorporated herein in its entirety. Nucleic and amino acid sequences accessible via Accession No. NM_001130851 [defined as *Homo sapiens* cyclin-dependent kinase inhibitor 3 (CDKN3) transcript variant 2, mRNA] are designated SEQ ID NO: 3 and 4, respectively.

Additional information pertaining to the human CDKN3 gene can be accessed via the worldwide web site maintained by the UCSC Genome Bioinformatics site [Reference No. Human Gene CDKN3 (uc001xar.3)].

PTPRG

Protein tyrosine phosphatase receptor comprises an extracellular region, a single transmembrane region, and two tandem intracytoplasmic catalytic domains, and thus represents a receptor-type PTP. Its extracellular region comprises a carbonic anhydrase-like (CAH) domain, which is also found in the extracellular region of another receptor-type PTP, PTPRBETA/ZETA. The PTPRBETA/ZETA gene is located in a chromosomal region that is frequently deleted in renal cell carcinoma and lung carcinoma, and is thus thought to be a candidate tumor suppressor gene.

The NCBI Reference Sequences corresponding to human PTPRG are as follows: NM_002841; NC_000003.11, NC_018914.1, and NT_022517.18, the entire content of each of which is incorporated herein in its entirety. Nucleic and amino acid sequences accessible via Accession No. NM_002841 [defined as *Homo sapiens* protein tyrosine phosphatase, receptor type, G (PTPRG), mRNA] are designated SEQ ID NO: 5 and 6, respectively.

Additional information pertaining to the human PTPRG gene can be accessed via the worldwide web site maintained by the UCSC Genome Bioinformatics site [Reference No. Human Gene PTPRG (uc003dlb.3)].

SLC39A13

SLC39A13 is one of 14 human members of the solute carrier transporter family 39 (SLC39), also referred to as ZIPs, that function in the uptake of zinc and other metals into the cytoplasm (Guerinot. Biochim Biophys Acta 2000; 1465 (1-2):190-198; Taylor et al. Biochim Biophys Acta 2003; 1611(1-2):16-30). In mammals, most of the ZIP proteins fall into one of two subfamilies, subfamily II (3 members) or LIV-1 (9 members). The human SLC39A13 gene encodes ZIP13, a member of the LZT (LIV-1 subfamily of ZIP zinc transporters) family. SLC39A13 knock out mice studies have revealed that SLC39A13/ZIP13 plays a crucial role in connective tissue development, at least in part due to its involvement in BMP/TGF-beta signaling pathways (Fukada et al. PLoS One 2008; 3(111):e3642). The importance of ZIP13 is connective tissue development is underscored by the finding that loss of function of ZIP13 is causative for the spondylocheiro dysplastic form of Ehlers-Danlos syndrome. Detailed biochemical characterization of the human ZIP13 protein has, moreover, revealed that ZIP13 contains eight putative transmembrane domains and a unique hydrophilic region and is positioned such that both its N and C termini face the luminal side on the Golgi. Additional analyses suggest that ZIP13 protein may form homodimers. ZIP13 has also been shown to mediate zinc influx (Bin et al. J Biol Chem 2011; 286(46):40255-65). The NCBI Reference Sequences corresponding to human SLC39A13 are as follows: NM_001128225; NC_000011.9, NC_018922.1, and NT_009237.18, the entire content of each of which is incorporated herein in its entirety.

Nucleic and amino acid sequences accessible via Accession No. NM_001128225 [defined as *Homo sapiens* solute carrier family 39 (zinc transporter), member 13(SLC39A13), transcript variant 1, mRNA] are designated SEQ ID NO: 7 and 8, respectively.

Additional information pertaining to the human SLC39A13 gene can be accessed via the worldwide web site maintained by the UCSC Genome Bioinformatics site [Reference No. Human Gene SLC39A13 (uc009ylq.3)].

Other members of the SLC39 family have been implicated as having a role in psychiatric phenotypes. For example, a genome-wide analysis revealed that a nonsynonymous SNP (nsSNP), which refers to a SNP that changes the sequence of the protein encoded by a gene, in SLC39A8 has been shown to be associated with SCZ (Carrera et al. Biol Psychiatry 2012; 71:169-177; the entire content of which is incorporated herein by reference in its entirety). Meta-analysis of two genome-wide association studies (GWAS) and additional studies have implicated SLC39A3 in bipolar disorder (Baum et al. Mol Psychiatry 2009; 13:466-467; 011ila et al. Mol Psychiatry 2009; 14:351-353). SLC39A11 has also been implicated in major depressive disorder (Muglia et al. Mol Psychiatry 2010; 15:589-601). Given the above, maintenance of metal ion homeostasis in the brain may be a significant factor in psychiatric illness. Differential expression patterns of the different SLC39 family members and the functional significance of mutations therein (e.g., enhanced function or impaired function) are likely to dictate whether or not psychiatric disease may arise as a result.

TGM5

TGM5 is a member of the transglutaminase family, which comprises TG1, TG2, TG3, TG4, TG5, TG6, TG7, and coagulation factor XIII. In the presence of Ca2+, transglutaminases may become catalytically active and participate in the formation of inter- and intra-molecular γ-glutamyl-ε-lysine bonds, also called iso-peptide bonds, between the side chains of peptidic glutamine and lysine. This typically generates high-molecular weight protein aggregates. Transglutaminases 1, 3 and 5 are mainly involved in skin-formation, factor XIII (plasma-transglutaminase) is active in blood coagulation and wound healing, transglutaminase 6 has mainly been found in neuronal tissues and transglutaminase 4 in semen fluid. Transglutaminase 2 (tissue transglutaminase, TG2) is ubiquitously present in various tissues. The NCBI Reference Sequences corresponding to human TGM5 are as follows: NM_004245; NC_000015.9, NC_018926.1, and NT_010194.17, the entire content of each of which is incorporated herein in its entirety.

Nucleic and amino acid sequences accessible via Accession No. NM_004245 [defined as *Homo sapiens* transglutaminase 5 (TGM5), transcript variant 2, mRNA] are designated SEQ ID NO: 9 and 10, respectively.

Additional information pertaining to the human TGM5 gene can be accessed via the worldwide web site maintained by the UCSC Genome Bioinformatics site [Reference No. Human Gene TGM5 (uc001zre.2)].

As indicated herein above, mutations in the gene for TGM5 have been causally related to acral peeling skin syndrome (APSS), an autosomal recessive skin disorder characterized by acral blistering and peeling of the outermost layers of the epidermis. See, for example, Pigors et al. J Invest Dermatol 2012, 132:2422-9. This is an intriguing finding and implicates the mutated amino acids as important in TGM5 protein structure and/or function critical to its role in cross-linking cornified cell envelope proteins. As described in Pigors et al., the TGM5 mutation includes p.M1T, p.L41P, p.L214CfsX15, p.S604IfsX9, and p.G113C. This study also revealed that the expression and distribution of several epidermal differentiation markers and corneodesmosin (CDSN) are altered in APSS keratinocytes and skin. Keratin 1, keratin 10, involucrin, loricrin, and CDSN were all upregulated in APSS keratinocytes and skin, possibly due to compensatory mechanisms for stabilization of the epidermal barrier. It is noteworthy, however, that TGM5 mutations have not been found in some cases of APPS. See, for example, Pavlovic et al. Pediatr Dermatol 2012, 29:258-63.

The aforementioned SNVs in CDKN3/KAP, BTK, PTPRG, SLC39A13, and TGM5 were identified during the course of genetic and epidemiologic investigations to assess the influence of paternal age on risk of schizophrenia in a population of subjects referred to herein as the Jerusalem Perinatal Study (JPS) cohort (Malaspina et al. Archives General Psychiatry. 2001; 58(4): 361-7; Malaspina et al. Schiz Bull 2001; 27(3) 379-393). The JPS cohort offers unequalled opportunities to discover genes predisposing to schizophrenia. The size of the cohort (92,000 births), their current ages (30-42 years), and the demonstrated influence of paternal age on risk yielded ~70 cases with fathers >45 years, of whom 11 complete trios (proband and both parents) provided blood samples for genetic analysis yielding these 5 mutations. These cases are the subjects of studies of de novo mutations as described herein. In addition, parents (if still living) and siblings are also available, and a very large amount of relevant prenatal, social, and clinical information has been collected. No other cohort in the world offers this combination of features.

Other systemic whole-genome analyses have been performed to assess the contibution of de novo protein-altering mutations (nsSNPs) to sporadic SCZ. See, for example, Xu et al. (Nature Genetics 2011; 43:864-869). It is noteworthy that although the analyses performed by Xu et al. identified de novo protein-altering mutations in 40 genes, mutations in any one of CDKN3/KAP, BTK, PTPRG, SLC39A13, or TGM5 were not identified. These distinctions likely underscore the nature of the analyses described herein, including: a large starting sample size and access to closely related non-SCZ relatives of SCZ patients as controls for comparison, which features confer sensitivity of detection.

De novo mutations have been shown in association with schizophrenia and autism. The mutations found in association with advancing paternal age may benefit from the expansion of clones of spermatogonia as men age, also conferrring cell cycle advancing or dysregulating effects on the offspring who inherit these mutated sperm.

Advanced Paternal Age and Schizophrenia. A steady increase in SCZ risk has been linked to advanced paternal age (Malaspina et al. Archives General Psychiatry. 2001; 58(4): 361-7; Sipos et al. BMJ 2004; 329:1070; El-Saadi et al. Schizophr. Res. 2004; 67:227-236; Zammit et al. Br. J. Psychiatry 2003; 183:405-408; Byrne et al. Arch. Gen. Psychiatry 2003; 60:673-678; Dalman et al. Am. J. Psychiatry 2002; 159:1591-1592; Brown et al. Am. J. Psychiatry 2002; 159:1528-1533; Tsuchiya et al. Schizophr. Res. 2005; 76:337-342). These findings are affirmed by epidemiological evidence. There is a "dosage effect" of increasing paternal age on the risk for SCZ and each study shows a tripling of risk for the offspring of the oldest fathers (>45-55 years). The studies were methodologically sound; they used prospective exposure data and validated diagnoses and controlled for every conceivable confound, including family history, maternal age, parental education and social ability, social class, birth order, birth weight and birth complications. Furthermore, the risk from advanced paternal age is specific for SCZ, vis-à-vis other psychiatric disorders, which is not the case for any other SCZ risk factor (including most genes). The present inventors have also shown biological plausibility for late paternal age to influence neural functioning in translational studies. First, two cohorts of 129S6/SvEv inbred mice showed reduced learning, exploration, and other measures for offspring of older sires (Bradley-Moore et al. 2002, Modeling Advanced Paternal Age on Progeny Behavior in Mice. Int. Soc Dev Psychob., published abstract). Second, a pattern of normal verbal and impaired performance IQ was associated with older paternal age in military data on 50,000 adolescents from our cohort (Malaspina et al. Psychiatr Genet. 2005; 15(2):117-25), a pattern we also found in New York, in sporadic cases with paternal age >33 (Malaspina et al. CNS Spectrums 2002; 7(1): 25).

Paternal age and rates of de novo mutations. As indicated above, the influence of paternal age on risk of schizophrenia in offspring has been demonstrated in several studies, including the JPS cohort (Hare and Moran 1979; Malaspina et al. Archives General Psychiatry. 2001; 58(4): 361-7; Brown et al. Am. J. Psychiatry 2002; 159:1528-1533; Zammit et al. Br. J. Psychiatry 2003; 183:405-408; Sipos et al. BMJ 2004; 329:1070; Tsuchiya et al. Schizophr. Res. 2005; 76:337-3). This association may reflect an increased frequency of de novo genetic mutations and/or epigenetic alterations in the paternal germ line (Penrose 1955). Such alterations would appear in all cells of the offspring, and genetic mutations could be transmitted to subsequent generations. As reviewed by Crow (2000), "the germline mutation rate in human males, especially older males, is generally much higher than in females, mainly because in males there are many more germ-cell divisions." Female germ cells do not undergo mitotic divisions after a girl's birth; in contrast, every male germ cell divides every 16 days after a boy's puberty. Consequently, DNA in the sperm of a 20-year-old father has been replicated 150 times, while DNA in the sperm of a 50-year-old father has been replicated 840 times. In early human evolution, probably very few males lived to reproduce in their 40s, so these features of male germ cell development would not have suffered any selective disadvantage.

Sperm vulnerability to increasing mutation frequency with age is associated with strong paternal age effects for progeria, multiple endocrine neoplasia 2A and 2B, and for Apert, Marfan, Crouzon, Waardenburg, and basal cell nevus syndromes (Risch et al. Am. J. Hum. Genet. 1987; 41:218-248). Paternal age effects have also been reported for several complex traits, including congenital heart defects (Olshan et al. Teratology 1994; 50:80-84), prostate cancer (Zhang et al. The Framingham Study. Am. J. Epidemiol. 1999; 150:1208-1212), cerebral palsy (Fletcher et al. J. Med. Genet. 1993; 30:44-46), sporadic Alzheimer disease (Bertram et al. Neurogenetics. 1998; 1:277-280), pre-eclampsia (Harlap et al. Epidemiology 2002; 13:660-667), multiple sclerosis (Montgomery et al. Epidemiology 2004; 15:717-723), spontaneous abortion (Nybo Andersen et al. Am. J. Epidemiol. 2004; 160:1214-1222; Slama et al. Am. J. Epidemiol. 2005; 161: 816-823) and schizophrenia. These effects suggest that for these complex conditions, a proportion of cases may be due to paternally inherited genomic mutations or epigenetic events.

Most paternal age effects leading to disease characterized thus far at the molecular level are point mutations (Crow. 2000, Nature Reviews 1:40-47). Is advanced paternal age also associated with higher rates of other sorts of mutations: genomic deletions or insertions, chromosomal abnormalities, repeat expansions, and so on? The influence of paternal age on rates of mutations other than base substitutions is heterogeneous with respect to mutation type and possibly with respect to target gene. The rate of occurrence of expanded repeat mutations may be paternally influenced. For example, for Huntington's disease, paternally derived triplet expansions are longer than maternally derived triplet expansions (Duyao et al. Nat Genet. 1993; 4:387-392). Furthermore, rates of insertion-deletion mutations at microsatellite markers are higher in paternal lineages than in maternal lineages (Kodaira et al 1995; Ellegren. Nat Genet. 2000; 24:400-402; Xu et al 2000). Also, mutation rates at Y-linked microsatellites appear to be associated with paternal age (Andreassen et al. Electrophoresis 2002; 23:2377-2383).

Current genomic technology now permits the identification of chromosomal deletions and duplications (i.e. copy number variants) of even a few thousand base pairs (Sebat et al. Science 2004; 305:525-528). It is not yet clear whether such mutations occur as de novo events more frequently among older fathers. Because such mutations may be important for neurodevelopmental disorders, the present inventors analyzed de novo copy-number variants in schizophrenia cases from the JPS born to older fathers.

Representational oligonucleotide microarray analysis (ROMA) was developed to scan the genome at high resolution in order to detect changes in gene copy numbers resulting from deletions and amplifications. ROMA was first used to identify genetic mutations in cancer cells (Lucito et al. Genome Res. 2003; 13:2291-2305) and has since been used to demonstrate that copy number polymorphisms (CNPs) are a common source of human genetic variation (Sebat et al. Science 2004; 305:525-528). CNP intervals impact genes involved with brain development and cell growth regulation, and frequently involve genomic regions where chromosomal rearrangements are known to occur. Benign CNPs have been identified on all chromosomes. ROMA has also been used to define the boundaries of rare cytogenetic rearrangements (Jobanputra et al. Genet Med. 2005; 7:111-118). The application of ROMA to detection of germline spontaneous mutations in schizophrenia is described herein.

Epigenetic alterations in children born to older fathers. There has been great interest recently in the possible influences of epigenetic alterations on schizophrenia (e.g. Jiang et al. Zhonghua Yi. Xue. Yi. Chuan Xue. Za Zhi. 2004; 21:376-378; Abel. Br. J. Psychiatry 2004; 184:383-385; Wong et al. Schizophr. Res. 2005; 78:137-146). Intriguing experimental data supports this interest. In rodents, age is associated with increased methylation of DNA in sperm (Oakes et al 2003). Also, methylation in mouse embryonic cortical neurons is associated with down-regulation of reelin and GAD67. This effect can be blocked by down-regulation of DNA methyltransferase I (DnmtI) (Noh et al. Proc. Natl. Acad. Sci. U.S.A 2005; 102:1749-1754). Hypothetically, then, either an epigenetic effect (methylation of the target gene) or a genetic effect (mutational loss of function of DNMTI) could lead to altered expression in the brain of genes critical to neuronal migration and synaptogenesis. Epigenetic events may lead to the discovery of nongenetic, as well as genetic, causes of disease. For example, experimental evidence suggests that maternal diet influences gene methylation (Lillycrop et al 2005). That is, the phenotype of gene methylation could arise from an environmental cause.

Genomic imprinting is a form of epigenetic modification. Genomic imprinting involves parent-of-origin-specific allelic silencing. Thus far, imprinting at 48 genes has been identified in humans. Inherited loss of imprinting is known to lead to neurodevelopmental disorders including Beckwith-Wiedeman syndrome, Prader-Willi syndrome and reciprocally Angelman syndrome, Rett Syndrome, and predisposition to colon cancer (Bjornsson et al. Trends Genet. 2004; 20:350-358). Imprinted genes play an important role in fetal development (Tycko et al. J. Cell Physiol 2002; 192:245-258). Many imprinted genes are expressed in brain, and evidence from mouse suggests that the hippocampus may be a particular locus of imprinted gene activity (Davies et al. Nat Genet. 2005; 37:625-629). It is an appealing hypothesis that loss of normal imprinting of genes critical to neurodevelopment may play a role in schizophrenia. Either methylation or histone acetylation (and probably other mechanisms) can lead to loss of imprinting. A major challenge of genomics is development of methods to detect changes that regulate gene expression.

Rare mutations in important genes. All de novo events share one feature: each is very likely to be individually rare, because each is the result of a single event in a single paternal germline. Certainly, hotspots for mutation exist (Bellus et al 1995), but de novo events influencing schizophrenia are likely to occur at many sites in many genes. Our screening strategy is robust to this heterogeneity, because the individual case is the unit of analysis. Thus we could detect either individually rare or common events.

It is important to identify individually rare events, because genes harboring one disease-predisposing allele are likely to harbor many more. In the presence of allelic and locus heterogeneity, this strategy enables one to identify genes in which to search for multiple mutations. Thus, finding a rare mutation in one case suggests that one may find other mutations in that gene in other cases.

The paternal age effect in the JPS cohort as a whole. There is emerging support for the idea that advanced paternal age increases the risk for a form of sporadic SCZ (Malaspina et al. CNS Spectr. 2002; 7(1):26-9; Byrne et al. Arch. Gen. Psychiatry 2003; 60:673-678; Sipos et al. BMJ 2004; 329: 1070). For each decade of paternal age, Sipos found no increase in the relative risk (RR) for familial SCZ (0.91: 0.44, 1.89), whereas the RR was significantly elevated for sporadic SCZ (1.60: 1.32, 1.92). Indeed, the offspring of the oldest fathers had a 5.5 fold risk for sporadic SCZ vs. that of the youngest fathers. The sporadic SCZ associated with late paternal age could have distinct genetic underpinnings. This contention is indirectly supported by genetic studies which showed that sporadic SCZ was not linked with "at risk haplotypes" in the genes for dystrobrevin-binding protein (Van Den Bogaert et al Am. J. Hum. Genet. 2003; 73:1438-1443) and neuregulin 1(Williams et al. Mol. Psychiatry 2003; 8:485-487), as were familial cases.

The present findings demonstrate that there is a linear effect of advancing paternal age effect on the risk for SCZ. Each decade multiplied the risk of SCZ by 1.4 (1.2-1.7, $p<0.0001$), so the relative risk for offspring of fathers aged 45+ was 3.0 (1.6-5.5) vs. fathers age 20-24, after control of maternal age. The attributable risk (or proportion) for paternal age in this cohort is large, 26%; suggesting that it could play a role in a substantial proportion of cases. In a New York clinical sample, cluster analyses identified a homogeneous phenotype in ~30% of cases associated with later paternal age, suggesting that the variant is common in clinical samples.

Although not wishing to be bound by theory, the present inventor proposes that the mutated genes identified herein as correlated with SCZ may be linked functionally to abnormalities in cell cell connectivity, due to cell cycle abnormalities. Alternatively, and/or additionally the present inventor proposes a role in inflammation and the endothelium. Systemic inflammation and/or endothelial abnormalities from this genetic susceptibility and gene-environment interaction affecting brain vasculature is a feasible pathophysiological mechanism proposed herein for these genes. This stands in marked contrast to those genes identified by Gulsiner et al. (2013, Cell 154:518-529; the entire content of which is incorporated herein by reference), which are involved in prefrontal cortex development. As described herein and in, for example, Muller et al. (2012, Advances in Protein Chemistry and Structural Biology 88:49-68), inflammation plays a role in SCZ, as demonstrated by evidence derived from clinical studies with COX-2 inhibitors showing that anti-inflammatory agents may be useful therapeutic agents for SCZ, particularly in the early stages of disease. Further to this point, signs of inflammation have been noted in schizophrenic brains (see, for example, Korschenhausen et al. 1996, Schizophrenia Research 19:103-109) and Bechter proposed the term "mild localized chronic encephalitis" to describe a slight, but chronic inflammatory process observed in schizophrenia. See Bechter. 2001, Neurology, Psychiatry and Brain Research 9, 55-70.

Further to the above, inhibitors of BTK have been proposed to be useful for treating allergic, autoimmune, and/or inflammatory diseases such as systemic lupus erythematosis, rheumatoid arthritis, and idiopathic thrombocytopenic purpura, as well as various cancers. See, for example, WO 2013/067264; Abdel-Magid (2013, ACS Medicinal Chemistry Letters 4:690-691); Hsu et al. (2013, Immunology Letters 150:97-104); and Uckun et al. (2010, Expert Opin Ther Patents 20:1457-1470, see in particular Table 2 therein which refers to references pertaining to BTK inhibitors), the entire content of each of which is incorporated herein by reference.

Along the same lines, PTPRG is upregulated by cytokines in astrocytoma cells, suggesting that it may be involved in inflammatory diseases of the brain. As revealed by results presented herein, two phosphatases, CDKN3/KAP and PTPRG, are mutated such that the mutation is predicted to increase PTP activity of the mutated PTP relative to the corresponding wildtype PTP. In keeping with a role for PTPs in inflammation, anti-inflammatory compounds, such as BAY-11-7082, have recently been shown to act as inhibitors of protein tyrosine phosphatases. See, for example, Krishnan et al. (2013, FEBS Journal 280:2830-2841). Taken together, these findings suggest that administering PTP inhibitors to SCZ patients might confer therapeutic benefit to the patients.

In view of the above, at least three of the five mutated genes and corresponding proteins are known to be involved in inflammatory pathways and thus, modulating their activity, as proposed herein, could reduce the chronic inflammation detected in schizophrenic brains and thereby confer therapeutic benefit to subjects afflicted with SCZ. It is, moreover, envisioned that agents that modulate any one of the five mutated proteins associated with SCZ may be administered in conjunction with therapeutic agents routinely used for treating SCZ, including, for example, typical antipsychotics [e.g., chlorpromazine (Thorazine), haloperidol (Haldol), perphenazine (Etrafon, Trilafon), and Fluphenazine (Prolixin)] and atypical antipsychotics [e.g., clozapine (Clozaril), risperidone (Risperdal), olanzapine (Zyprexa), quetiapine (Seroquel), ziprasidone (Geodon), aripiprazole (Abilify), and paliperidone (Invega)].

Definitions

Various terms relating to the molecules and methods of the present invention are used hereinabove and also throughout the specifications and claims.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

A "vector" is a replicon, such as plasmid, phage, cosmid, or virus into which another nucleic acid segment may be operably inserted so as to bring about the replication or expression of the segment.

An "expression vector" is a vector which (due to the presence of appropriate transcriptional and/or translational control sequences) is capable of expressing a DNA molecule which has been cloned into the vector and of thereby producing an RNA or protein product encoded by an expressible gene provided by said DNA. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, when a eukaryotic expression vector is employed, e.g., for genetic manipulation prior to gene delivery, then the appropriate host cell would be any eukaryotic cell capable of expressing the cloned sequences.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like. The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on to or inherited by progeny cells or organisms of the recipient cell or organism. In other applications, the introduced nucleic acid may exist in the recipient cell or host organism only transiently.

The term "substantially pure" refers to a preparation comprising at least 50-60% by weight of the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide or amino acid means a sequence having the properties of a given SEQ ID NO:. For example, when used in reference to an amino or nucleic acid sequence, the phrase includes the sequence per se and molecular modifications that would not affect the basic and novel characteristics of the sequence. With regard to the diagnostic sequences of the present invention, for example, the phrase includes the sequence per se and molecular modifications that would not appreciably affect the ability of the mutation identified to alter functional activity of a protein encoded thereby.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (Altschul et al., 1990, J Mol Biol 215:403-410) using a gapped alignment with default parameters, may be used to determine the level of identity and homology between nucleic acid sequences and amino acid sequences.

With respect to single stranded nucleic acids, particularly oligonucleotides, the terms "specifically hybridizing" or "specifically annealing" refer to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "functional" as used herein implies that the nucleic or amino acid sequence is functional for the recited assay or purpose.

The term "schizophrenia" or "SCZ" as used herein may be used to refer to the SCZ-spectrum disorders, Schizotypal Personality Disorder (SPD) and Schizoaffective Disorder (SD), as well as Schizophrenia under the narrower, DSM-IV definition and even to affective psychoses.

As used herein, a "haplotype" is one or a set of markers (e.g., polymorphisms) that are grouped closely together on a given chromosome and are usually inherited as a group. As used herein, the term "polymorphism" refers to the condition in which there is a variation in the DNA sequence between some members of a species. A haplotype can include, but not be limited to, a variety of genetic markers, including indels (insertions or deletions of the DNA at particular locations on the chromosome); single nucleotide polymorphisms (SNPs) in which a particular nucleotide is changed; microsatellites; and minisatellites.

The term "mutant specific amplification product" as used herein refers to a product generated by an amplification reaction from a nucleic acid sequence comprising a mutation at a specific position in the nucleic acid sequence, wherein the presence of the mutation is correlated with schizophrenia.

The term "biologically compatible salt solution" is used herein to describe any salt solution in which nucleic acid sequences may be stably maintained. For applications wherein nucleic acid sequences in such salt solutions are to be amplified, such salt solutions are modifiable (e.g., capable of being diluted or altered to change substituent concentration) to be compatible with polymerase activity and the like.

In an embodiment, the method comprises obtaining a sample of a tissue or a body fluid from the subject (e.g., a mammal). Non-limiting examples of tissue or body fluids that can be used include blood, plasma, lymph, buccal cells, and tissue biopsies.

The sample of the tissue or body fluid from the mammal or nucleic acid sequences isolated therefrom can be sequenced or can be contacted with a composition comprising a PCR primer pair that flanks a mutation identified herein that is associated with SCZ and a biologically compatible salt solution. Mutation specific primers are also envisioned herein. To improve the sensitivity of a PCR-based assay, one or both primers of a PCR primer pair used to amplify a nucleic acid sequence comprising a mutation associated with SCZ may be fluorescently tagged or labeled. Primers may, for example, be labeled with 6'-FAM. PCR amplification products generated using such fluorescently labeled primers are, therefore, fluorescently labeled and detectable using equipment designed to detect fluorescent emissions. An ABI 310 Genetic Analyzer and Genescan 3.1.2 software (Applied Biosystems), for example, may be used for these analyses.

The sample can be contacted with the composition comprising at least one PCR primer pair as indicated above by any means routinely applied for contacting a sample with PCR primer pairs. For example, in one embodiment, the sample and the composition are contacted in a microwell plate or in a microvial adapted for the mixture of small volumes.

A number of methods are available for analysis of variant (e.g., mutant or polymorphic) nucleic acid sequences. Assays for detection variants (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. Assays may be performed in combination or in hybrid (e.g., different reagents or technologies from several assays are combined to yield one assay). The following assays are useful for detecting mutations identified as associated with SCZ.

Direct Sequencing Assays

Variant sequences can be detected using a direct sequencing technique. In accordance with such an approach, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNV or mutation of interest) is sequenced using any suitable method, including but not limited to manual sequencing using radioactive marker nucleotides or automated sequencing. The results of the sequencing are analyzed using techniques known in the art. The sequence is examined and the presence or absence of a given SNV or mutation is determined.

PCR Assays

Variant sequences can also be detected using a PCR-based assay. As indicated herein above, PCR assays may comprise oligonucleotide primers that hybridize to regions of the specified nucleic acids that flank one of the SNVs identified herein as associated with SCZ. Primers for such purposes are selected for their specificity and position relative to the SNV. In a particular embodiment, a PCR product generated in such an assay will be 50-2000 base pairs (bps) in length. In a more particular embodiment, a PCR product generated will be 100-800 bps in length. The size of the PCR product is not critical as long as it encompasses the SNV (if mutated) or wildtype sequence (if wildtype or non-mutated) and can be generated easily and can be analyzed thereafter. A PCR product so generated can then be sequenced using standard techniques to determine if the PCR product comprises a mutated or wildtype sequence at the SNV site. Alternatively, PCR assays may comprise oligonucleotide primers that hybridize only to the variant or wild type allele of a nucleic acid comprising one of the SNVs associated with SCZ described herein. Both sets of primers are used to amplify individual samples of DNA. If the mutant primers result in a PCR product, then the patient has the mutant in question. If the wild-type primers result in a PCR product, then the patient has the wild type sequence.

In keeping with standard IUPAC codes, the single letter designations used in connection with the primer pairs listed below are as follows: "K" stands for G or T; "R" stands for A or G; and "Y" stands for C or T.

In a particular embodiment, exemplary primers for amplifying the region of CDKN3, wherein the identified mutant [mutant coordinates 54,878,244; the mutation being G>G/T (K)] is found are as follows: left primer, AGACCCCTTTT-GATTCAGACA (SEQ ID NO: 11); right primer, AAGGTTTTTCGGTAATTTTTAAGG (SEQ ID NO: 12). A PCR amplification may be performed using an annealing temperature of about 58° C. An amplification product generated using this primer pair will be about 383 base pairs (bp). In that the aforementioned CDKN3 primers flank the mutation site, analysis of the amplification product by, for example, sequencing or differential hybridization can be used to determine if the mutation is present or not.

In another particular embodiment, exemplary primers for amplifying the region of SLC39A13, wherein the identified mutant [mutant coordinates 47,435,184, the mutation being G>A/G (R)] is found are as follows: left primer, CTCAATG-GAGGCCACTGTCT (SEQ ID NO: 13); right primer, ATGGGGGATGAGAGCCTTAG (SEQ ID NO: 14). A PCR amplification may be performed using an annealing temperature of about 60° C. An amplification product generated using this primer pair will be about 380 base pairs (bp). The technique and set up for next generation sequencing was as follows: HIGH guanine cytosine (GC); common 89 bp insertion deletion (indel) located within amplicon. In that the aforementioned SLC39A13 primers flank the mutation site, analysis of the amplification product by, for example, sequencing or differential hybridization can be used to determine if the mutation is present or not.

In another particular embodiment, exemplary primers for amplifying the region of PTPRG, wherein the identified mutant [mutant coordinates 62,180,781, the mutation being C>C/T (Y)] is found are as follows: left primer, TCCCAGGGAAGCT-CATAAAA (SEQ ID NO: 15); right primer, GCCGA-TAAAACCTCCAACCT (SEQ ID NO: 16). A PCR amplification may be performed using an annealing temperature of about 60° C. An amplification product generated using this primer pair will be about 488 base pairs (bp). In that the aforementioned PTPRG primers flank the mutation site, analysis of the amplification product by, for example, sequencing or differential hybridization can be used to determine if the mutation is present or not.

In another particular embodiment, exemplary primers for amplifying the region of BTK, wherein the identified mutant [mutant coordinates 100,615,568, the mutation being C>C/T (Y)] is found are as follows: left primer, TATGTGC-CCAACAACAGAGG (SEQ ID NO: 17); right primer, GCCAGAGAGTTGGGAGAGAA (SEQ ID NO: 18). A PCR amplification may be performed using an annealing temperature of about 60° C. An amplification product generated using this primer pair will be about 475 base pairs (bp). In that the aforementioned BTK primers flank the mutation site, analysis of the amplification product by, for example, sequencing or differential hybridization can be used to determine if the mutation is present or not.

Additional primer pairs and conditions useful for amplifying BTK include those listed in Table 2 of Hashimoto et al. (1996, Blood 88:561-573; the entire content of which is incorporated herein by reference).

In another particular embodiment, exemplary primers for amplifying the region of TGM5, wherein the identified mutant [mutant coordinates 43,552,271, the mutation being G>G/T (K)] is found are as follows: left primer, TCTGTT-TAAGCAAAGATGATTTGG (SEQ ID NO: 19); right primer, AGGGCCTCAGCTCTACTTCC (SEQ ID NO: 20). A PCR amplification may be performed using an annealing temperature of about 60° C. An amplification product generated using this primer pair will be about 499 base pairs (bp). In that the aforementioned TGM5 primers flank the mutation site, analysis of the amplification product by, for example, sequencing or differential hybridization can be used to determine if the mutation is present or not.

The aforementioned primer pairs were used to verify that each of the five de novo mutations in a JPSS trio was real in the affected child and absent from both parents.

Variant sequences can also be detected using techniques such as single PCR multiplex SNaPshot™ reactions such as those described in, for example, Di Christofaro et al. (2010, J Molec Diag. 12:453-460; the entire content of which is incorporated herein by reference).

Mutational Detection by dHPLC

Variant sequences can also be detected using a PCR-based assay with consecutive detection of nucleotide variants by dHPLC (denaturing high performance liquid chromatography). Exemplary systems and Methods for dHPLC include, but are not limited to, WAVE (Transgenomic, Inc; Omaha, Nebr.) or VARIAN equipment (Palo Alto, Calif.).

Fragment Length Polymorphism Assays: Variant sequences can also be detected using a fragment length polymorphism assay. In such assays, a unique DNA banding pattern based on cleaving the DNA at a series of positions is generated using an enzyme (e.g., a restriction enzyme or a CLEAVASE I (Third Wave Technologies, Madison, Wis.) enzyme). DNA fragments from a sample containing a SNP or a mutation will have a different banding pattern than wild type.

RFLP Assay: Variant sequences can also be detected using a restriction fragment length polymorphism assay (RFLP). The region of interest is first isolated using PCR and PCR products are then cleaved with restriction enzymes known to produce a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

CFLP Assay: Variant sequences can also be detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). CFLP is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNV or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

Hybridization Assays

Variant sequences can also be detected using a hybridization assay. In hybridization assays, the presence or absence of a given SNV or mutation is determined based on the ability of the DNA from the sample to hybridize to a complementary DNA molecule (e.g., an oligonucleotide probe). A variety of hybridization assays using a variety of technologies for hybridization and detection are available. A description of a selection of assays is provided below.

Direct Detection of Hybridization: In some embodiments, hybridization of a probe to the sequence of interest (e.g., a SNV or mutation) is detected directly by visualizing a bound probe (e.g., a Northern or Southern assay; See e.g., Ausubel et al. (eds.), Current Protocols in Molecular Biology, John Wiley & Sons, NY (1991)). In these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNV or mutation being detected is allowed to contact the membrane under low, medium, or high stringency conditions. Unbound probe is removed and the presence of binding is detected by visualizing the labeled probe.

Detection of Hybridization Using "DNA Chip" Assays: Variant sequences can also be detected using a DNA chip hybridization assay. In this assay, a series of oligonucleotide probes are affixed to a solid support. The oligonucleotide probes are designed to be unique to a given SNV or mutation. The DNA sample of interest is contacted with the DNA "chip" and hybridization is detected. In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference in its entirety) assay. The GeneChip technology uses miniaturized, high-density arrays of oligonucleotide probes affixed to a "chip." Detailed protocols are described in the above references, but briefly, the nucleic acid to be analyzed is isolated, amplified by PCR, and labeled with a fluorescent reporter group. The labeled DNA is then incubated with the array using a fluidics station and analyzed using a scanner that can detect patterns of hybridization. Hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which is incorporated herein by reference in its entirety). In brief, DNA capture probes unique to a given SNV or mutation are electronically placed at, or "addressed" to, specific sites on the microchip. In brief, a test sample is analyzed for the presence of target DNA molecules by determining which of the DNA capture probes hybridize, with complementary DNA in the test sample (e.g., a PCR amplified gene of interest).

Array technologies based on the segregation of fluids on a flat surface (chip) by differences in surface tension (ProtoGene, Palo Alto, Calif.) can also be utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. DNA probes unique for the SNV or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference in its entirety). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNV or mutation. To perform an assay, the BEAD ARRAY is contacted with a prepared subject sample (e.g., DNA). Hybridization is detected using any suitable method.

Enzymatic Detection of Hybridization

Hybridization is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference in its entirety). The INVADER assay detects specific DNA and RNA sequences by using structure-specific enzymes to cleave a complex formed by the hybridization of overlapping oligonucleotide probes. The INVADER assay detects specific mutations and SNVs in unamplified genomic DNA. The isolated DNA sample is contacted with the first probe specific either for a SNV mutation or wild type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive and negative controls.

Hybridization of a bound probe can also be detected using a TaqMan assay (PE Biosystems, Foster City, Calif.; See e.g., U.S. Pat. Nos. 5,962,233 and 5,538,848, each of which is herein incorporated by reference in its entirety). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

Polymorphisms can also be detected using the SNP-IT primer extension assay (Orchid Biosciences, Princeton, N.J.; See e.g., U.S. Pat. Nos. 5,952,174 and 5,919,626, each of which is herein incorporated by reference in its entirety). In this assay, SNVs are identified using a specially synthesized DNA primer and a DNA polymerase to extend the DNA chain by one base at the suspected SNV location. DNA in the region of interest is amplified and denatured. Polymerase reactions are then performed using miniaturized systems called microfluidics. Detection is accomplished by adding a label to the nucleotide at the SNV or mutation location. Incorporation of the label into the DNA can be detected by any suitable method (e.g., if the nucleotide contains a biotin label, detection is via a fluorescently labeled antibody specific for biotin).

Mass Spectroscopy Assay

The MassARRAY system (Sequenom, San Diego, Calif.) can also be used to detect variant sequences (See e.g., U.S. Pat. Nos. 6,043,031; 5,777,324; and 5,605,798; each of which is herein incorporated by reference in its entirety) as described therein.

Detection of Variant CDKN3/KAP, BTK, PTPRG, SLC39A13, and TGM5 Proteins

In other embodiments, variant (e.g., truncated or mutated) CDKN3/KAP, BTK, PTPRG, SLC39A13, and TGM5 polypeptides are detected. Any suitable method may be used to detect truncated or mutant CDKN3/KAP, BTK, PTPRG, SLC39A13, and TGM5 polypeptides including, but not limited to, those described below.

Cell Free Translation: In some embodiments, cell-free translation methods developed by Ambergen, Inc. (Boston, Mass.) are utilized. Such methods are directed to labeling, detection, quantitation, analysis and isolation of nascent proteins produced in a cell-free or cellular translation system without the use of radioactive amino acids or other radioactive labels. One application of Ambergen's protein labeling technology is the gel free truncation test (GFTT) assay (See e.g., U.S. Pat. No. 6,303,337, herein incorporated by reference in its entirety). This assay can be used to screen for truncation mutations in, for example, PTPRG polypeptides. In the GFTT assay, a marker (e.g., a fluorophore) is introduced into the nascent protein during translation near the N-terminus of the protein. A second and different marker (e.g., a fluorophore with a different emission wavelength) is introduced into the nascent protein near the C-terminus of the protein. The protein is then separated from the translation system and the signal from the markers is measured. A comparison of the measurements from the N and C terminal signals provides information on the fraction of the molecules with a C-terminal truncation (i.e., if the normalized signal from the C-terminal marker is 50% of the signal from the N-terminal marker, 50% of the molecules have a C-terminal truncation).

Antibody Binding: Antibodies can also be used to determine if an individual contains an allele encoding a variant CDKN3/KAP, BTK, PTPRG, SLC39A13, or TGM5 gene. In preferred embodiments, antibodies that discriminate between variant (i.e., truncated or mutated proteins) and wild-type proteins are utilized. Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g. using colloidal gold, enzyme or radio-isotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In a particular embodiment, antibody binding can be determined by detecting a label on the primary antibody. Alternatively, the primary antibody is detected by detecting binding of a secondary antibody or reagent to the primary antibody. In a further embodiment, the secondary antibody is labeled. Many methods are known in the art for detecting binding in an immunoassay and are encompassed herein.

Pharmacogenetic Testing

"Pharmacogenomics," as used herein, refers to the application of genomics technologies to provide guidance with respect to therapeutic regimens, such that a therapeutic regimen can be specifically tailored or modified based on a particular patient's genome. The term may be used to refer to the study of how a patient's genes determine his or her response to a drug (e.g., a patient's "drug response phenotype," or "drug response genotype"). Thus, another aspect of the invention provides methods for tailoring an individual's therapeutic treatment according to that individual's drug response genotype, for example, a BTK haplotype status.

Information generated from pharmacogenomic research, such as that presented herein, can be used to determine appropriate dosage and treatment regimens for therapeutic treatment or prophylaxis of a subject in need thereof. Such knowledge, when applied to dosing or drug selection, can avoid adverse reactions or therapeutic failure and thus enhance therapeutic or prophylactic efficiency when administering a therapeutic composition to a patient, as a means of treating or preventing a psychotic disorder.

In one embodiment, a physician or clinician may consider applying knowledge obtained in relevant pharmacogenomics studies, such as those described herein, when determining whether to administer a pharmaceutical composition, e.g., an antipsychotic agent or a combination of antipsychotic agents, to a subject. In another embodiment, a physician or clinician may consider applying such knowledge when determining the dosage (e.g., amount per treatment or frequency of treatments) of a treatment (e.g., an antipsychotic agent or combination of antipsychotic agents) to be administered to a patient.

Information pertaining to a haplotype associated with an altered pharmacogenomic response for SCZ, such as those described herein, can be used to stratify or select a subject population for a clinical trial. The information can, moreover, be used to stratify individuals that are more likely to be non-responders from those who will be responders. The variant CDKN3/KAP, BTK, PTPRG, SLC39A13, and TGM5 haplotypes described herein can be used in pharmacogenomics-based design and to monitor, for example, a clinical trial.

Information pertaining to variant CDKN3/KAP, BTK, PTPRG, SLC39A13, and TGM5 haplotypes associated with an increased likelihood of SCZ or with altered pharmacogenomic response relative to non-SCZ subjects can also be used to stratify or select human cells or cell lines for drug testing purposes. Human cells are useful for studying the effect of a polymorphism on physiological function and for identifying and/or evaluating potential therapeutic agents for the treatment of SCZ. The information can, therefore, be used to separate cells that respond to particular drugs from those that do not respond and thus, identify therapeutic agents that may be prove useful as therapeutics. Such cell based assays may also be useful for identifying signaling pathways in cells comprising altered haplotypes that are altered relative to wildtype cells (that do not have the haplotype or haplotypes in question). The identification of such pathways may confer additional insight regarding the classes of agents that could be tested for therapeutic efficacy in regimens designed to treat SCZ patients.

Theranostics

As used herein, the word "theranostic" refers to a combination of a specific therapy and diagnostic. The combination utilizes a diagnostic test to identify a specific patient subtype(s) of psychotic disorders, e.g., SCZ, that have common genetic, clinical, metabolic, and/or prognostic features. By performing a diagnostic test, e.g. a genetic test to identify a variant CDKN3/KAP, BTK, PTPRG, SLC39A13, or TGM5 haplotype, a skilled practitioner can classify the patient into a specific disease sub-type or category. Such disease sub-types may include, for example, a BTK haplotype positive or negative subgroup. Patients designated as belonging to one or another of these sub-types would be predicted to respond to a given therapy in a particular manner.

Also included herein are compositions and methods for the identification and treatment of subjects who have an increased likelihood of having SCZ or have a particular sub-type of SCZ, such that a pharmacogenomic or theranostic approach can be taken to test such individuals to determine the effectiveness of a particular therapeutic intervention (e.g., a pharmaceutical as described herein) and/or to alter therapeutic intervention to enhance efficacy. Accordingly, methods and compositions described herein provide means to optimize treatment of a subject having or suspected of having a psychotic disorder such as SCZ. Provided herein is a pharmacogenomic or theranostic approach to treat or prevent a psychotic disorder such as SCZ, by integrating diagnostics and therapeutics to improve ongoing treatment of a subject. In essence, this means designing and implementing tests that identify which patients are best suited to a particular therapy, and providing feedback on how well a drug is working to optimize a treatment regimen.

Within a clinical trial setting, a theranostic method or composition as described herein can provide information on which basis trial design can be optimized, efficacy can be monitored, and drug safety can be enhanced. For instance, "trial design" theranostics can be used for patient stratification, assessment of patient eligibility (inclusion/exclusion), creation of homogeneous treatment groups, and selection of patient samples that are representative of the general population. Such theranostic tests can therefore maximize efficacy in patient populations examined and thus, minimize the number of individuals needed for trial recruitment. "Efficacy" theranostics are useful for monitoring therapy and assessing efficacy criteria. Finally, "safety" theranostics can be used to prevent adverse drug reactions or avoid medication error.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter of the disease. In yet another embodiment, "treating" or "treatment" refers to modulating the disease or disorder, either physically, (e.g., stabilization of a discernible symptom), physiologically (e.g., stabilization of a physical parameter), or both. In a further embodiment, "treating" or "treatment" relates to slowing the progression of the disease. With respect to alleviating symptoms of SCZ in a subject/patient, symptomatic relief would include, for example, a reduction in distorted perceptions of reality (hallucinations and delusions), social deficits, disorganized language and behavior, and mild cognitive dysfunction.

The phrase "pharmaceutically acceptable" refers to molecular entities and compositions which are suitable for use in contact with the tissues of human beings and animals without excessive toxicity, irritation, allergic response, or other problem or complication, commensurate with a reasonable benefit/risk ratio.

A "therapeutically effective amount" is an amount of a compound or agent described herein or a combination of two or more such compounds, which inhibits, totally or partially, the progression of the condition or alleviates, at least partially, one or more symptoms of the condition. The amount that is therapeutically effective will depend upon the patient's size and gender, the condition to be treated, the severity of the condition and the result sought. For a given patient, a therapeutically effective amount can be determined by methods known to those of skill in the art.

The term "cancer-free" refers to subjects or patients in whom no cancer has been detected.

According to another aspect, a pharmaceutical composition is envisioned herein that comprises a therapeutically-effective amount of one or more compounds described herein or a pharmaceutically-acceptable salt, ester or prodrug thereof, together with a pharmaceutically-acceptable diluent or carrier.

The compositions may be formulated for any route of administration, in particular for oral, rectal, transdermal, subcutaneous, intravenous, intramuscular, intraperitoneal, or intranasal administration. The compositions may be formulated in any conventional form, for example, as tablets, capsules, caplets, solutions, suspensions, dispersions, syrups, sprays, gels, suppositories, patches and emulsions.

In a particular embodiment, a compound or composition thereof is administered systemically. In a more particular embodiment, the compound or composition thereof is an oral small molecule or a formulation thereof suitable for intravenous or subcutaneous administration.

The compositions are administered in a manner compatible with the dosage formulation, and in a therapeutically effective amount. The quantity to be administered depends on the subject to be treated, capacity of the subject's immune system to utilize the active ingredient, and degree of inhibition or cell modulation desired. Precise amounts of active ingredient required to be administered depend on the judgment of the practitioner and are particular to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Animal Models

Overview of Mouse Model Recapitulating Mutants Identified in Human

Knock in and knock out models that recapitulate the change in function genes identified in the aforementioned Jerusalem study may be introduced into 129SvEv/Tac mice or other strains. Tests directed to assessing immune molecules in the brain and periphery, endothelial integrity, microvessel diameters, and metabolic measures may be performed in the knock in and knock out mice. Such methods are known in the art. Behavioral testing of the knock in and knock out mice may also be performed, as described herein, and in accordance with routine practice. Behavioral testing will commence at 12 weeks, described below. In further embodiments, antagonists of the gain-of function genes and their pathways may be administered to assess the effects on the behavioral abnormalities. Changes in gene expression and gene methylation will be compared between the gene knock out/in mice and intact, wildtype mice.

More particularly, at 12 weeks of age, the mice will undergo behavioral testing. The behavioral tasks may be administered with the least stressful tasks first and the most stressful last, in order to avoid any carry-over effects. Mice will receive one week of rest between each behavioral task. Behavioral testing will be performed during the light cycle.

Open Field (OF): The mice will be placed in the center of a large square (17×17×12 inches) plexiglas chamber under bright ambient light conditions (800 lux). Activity will be monitored in 5 min bins for 30 minutes using infrared beams. The measures recorded will include total ambulatory distance and time, vertical activity and center activity. The total distance covered during locomotion will be used as an index of activity, while the proportion of time spent or distance traveled in the center is taken as a measure of anxiety.

Startle Activity: Mice will be placed in acoustically isolated startle chambers (MED Associates). The test is initiated with a 5 min acclimation followed by three sessions of trials. The background noise will be 70 dB throughout the acclimation and trial periods. Sessions 1 and 3 will include 10 trials of startle stimuli (120 dB; 40 ms). Session 2 consists of 56 trials in which startle response magnitude (the area under curve), peak latency, and onset latency to each stimulus will be recorded for trials in which the startle stimulus will be presented alone or preceded by 100 ms with a 15 ms prepulse. The prepulse amplitude will be 2, 4, or 8 dB above background (Stefansson et al., 2002). Startle responses will be measured by the downward force (N) applied to a forcemeter between 30 and 70 ms after the onset of the startle stimulus. Animals failing to emit a reliable baseline startle response of at least 100 arbitrary units will be excluded. Prepulse inhibition (PPI) will be calculated as $1-(ppr[x]/sr)$, where $ppr[x]$ is the average startle response across trials presenting a prepulse of amplitude x, and sr is the average startle response across trials in which the startle stimulus will be presented alone.

Fear Conditioning: Fear conditioning will be conducted in chambers Med Associates (St. Albans, Vt.). A house light (CM1820 bulb) mounted directly above the chamber provides illumination. Each chamber will be located inside a larger, insulated plastic cabinet that provides protection from outside light and noise.

The fear conditioning procedure will be conducted over 3 days. On day 1, mice will be placed in the conditioning chamber and receive pairings between a tone (20 s, 80 dB, 2 KHz) and a coterminating shock (1 s, 0.5-0.7 mA). The whole procedure lasts 6 minutes and the tone-shock pairing will be separated by at least 60 s.

On day 2, the procedure and context are changed in several ways to test conditioned fear of the tone CS in the absence of contextual cues associated with shock. The floor and walls of the chamber will be covered by white and black plastic inserts and a smooth floor will be used; the chamber will also be scented with either limonene or menthol. No shock will be administered during this test. Each mouse will be placed in the chamber for 6 min and the same tone as on the previous day will be presented 3 times for 20 s at 120, 180 and 279 s into the session. Freezing will be scored for the 1 min before the first tone presentation (pretone freezing) and during the 20 s of each tone presentation (tone-elicited freezing).

On day 3, mice will be tested for conditioned fear of the training context. The testing procedure and context will be identical to those used on day 1, except the shock will be not presented.

Elevated Plus maze: The elevated plus maze has been described previously (Gross et al. 2002, Nature 416:396. The mice will be placed in the middle of a cross-shaped platform with two open arms and two closed arms for 6 minutes. Time and number of entries into open and closed arms will be measured by a trained observer blind to the gene-status of the mice.

Social Interaction: A modified version of the OF chamber will be used for this experiment, such that a smaller cage containing a confederate mouse will be suspended in one corner (social cage) and an empty cage will be placed in another corner (neutral cage). The mouse will be placed in the center of the chamber for 10 minutes. Time and quality of behavior in proximity to the caged confederate will be compared to time and behavior spent at the neutral cage, as well as in the empty quadrants of the OF chamber.

Statistical analysis of behavioral data. All behavioral data will be analyzed using student t-tests or repeated measure ANOVA. On the composite RANK scores, Chi-square tests will be performed.

Animal Models of Schizophrenia

Animals used as models for schizophrenia include rats, mice, and primates. Multiple animal models of schizophrenia exist and are used routinely in pre-clinical development of drugs.

There are four basic categories of models that simulate schizophrenic defects, which models include pharmacological models, developmental models, lesion models, and genetic models. Pharmacological models, also known as drug-induced models, are widely used and involve the manipulation of various neurotransmitter systems, including dopamine, glutamate serotonin, and GABA. Lesion models, wherein a particular area or region of an animal's brain is ablated, are based on theories that schizophrenia arises from neurodevelopmental defects and involves neurodegeneration. Rodent models of schizophrenia mostly display symptoms characteristic of positive symptoms of schizophrenia. Some rodent models do, however, also exhibit symptoms characteristic of negative symptoms.

Behavioral Traits

Prepulse inhibition (PPI): PPI refers to the inhibition of the response to a startling stimulus when the stimulus is preceded by a weaker stimulus. Abnormalities in PPI are seen in patients with SCZ.

Latent inhibition: Latent inhibition is a technical term used in classical conditioning to refer to the observation that a familiar stimulus takes longer to acquire meaning (as a signal or conditioned stimulus) than a new stimulus. In latent inhibition, frequent presentation of a stimulus leads to a reduced rate at which the stimulus produces meaning. Anomalies in latent inhibition have been linked with SCZ in acute events.

Paired click gating: In paired-click gating or P50 gating, a click which rapidly follows a previous click produces a reduced response. SCZ patient exhibit reduced gating relative to normal subjects.

Social withdrawal: One of the negative symptoms of schizophrenia is social withdrawal, which symptom has been modelled by socially isolating animals.

Locomotor traits: In that locomotor anomalies are often found in patients with SCZ, some locomotor changes, including sterotypy, are used to test the validity of animal models.

For a review describing the above behavioral traits, see, for example, Geyer et al. (2002, "Chapter 50: Animal Models Relevant to Schizophrenia Disorders". Neuropsychopharmacology: the fifth generation of progress. American College of Neuropsychopharmacology) and Jones et al. (2011, British J Pharmacol 164:1162-1194), the entire content of each of which is incorporated herein in its entirety.

Other Traits

Cortical volume: Reduced volume of the prefrontal cortex is an anatomical trait of schizophrenia patients which is used to test the validity of animal models.

NMDA receptor gene expression: Variations in the expression of the NR2B and NR1 subunits of the NMDA receptor are used to test developmental animal models.

Dopamine release: Neuroimaging studies on patients with schizophrenia have found increased dopamine release after treatment with amphetamine relative to normal controls.

For a review of the above other traits, see, for example, Geyer et al. (2002, "Chapter 50: Animal Models Relevant to Schizophrenia Disorders". Neuropsychopharmacology: the fifth generation of progress. American College of Neuropsychopharmacology) and Jones et al. (2011, British J Pharmacol 164:1162-1194), the entire content of each of which is incorporated herein in its entirety.

Pharmacological Models of SCZ

Dopamine: The dopamine hypothesis of SCZ postulates that the disease is caused by disturbed dopamine neurotransmission. Dopamine, a monamine neurotransmitter known to be involved in other diseases (such as, e.g., Parkinson's disease), has been implicated in SCZ because increased activity of the mesolimbic pathway, a dopaminergic pathway, has been observed in schizophrenia patients. More particularly, increased L-DOPA decarboxylase levels have been detected in the brains of these patients. L-DOPA decarboxylase is known to convert L-DOPA to dopamine by removing a carboxyl group. See, for example, Marcotte et al. (2001, J Psychiatry & Neuroscience 26:395-410; the entire content of which is incorporated herein by reference). Some animal models for SCZ are, therefore, based on drug-induced alterations of the dopaminergic system. See, for example, Jones et al. (2011, British J Pharmacol 164:1162-1194; the entire content of which is incorporated herein in its entirety)

Persistent treatment of rodents with amphetamine models some symptoms of schizophrenia, including: hyperactivity, enduring prepulse inhibition abnormalities, and cognitive abnormalities associated with the prefrontal cortex, including attention deficits. Neither negative symptoms, such as problems with social interaction or hippocampus-related deficits are observed in amphetamine rodent models. The antipsychotics clozapine and haloperidol reverse the effects of amphetamine on attention in rats. See, for example, Jones et al. (2011, British J Pharmacol 164:1162-1194).

Glutamate: Glutamate is the most abundant excitatory neurotransmitter in vertebrate nervous systems. Evidence for the involvement of glutamate in schizophrenia includes analogous symptoms which are produced by glutamate NMDA receptor antagonists such as phencyclidine (PCP) and ketamine. PCP is a non-competitive NMDA receptor antagonist which produces hallucinations and delusions in normal subjects. In rat models, disturbed cognition, deficits in social interaction, locomotor anomalies, and prepulse inhibition deficits are observed following acute administration of PCP. Evidence that persistent PCP use and abuse in humans results in lasting deficits beyond the period of treatment has led to the suggestion that this regime in rodents may be a more accurate model of schizophrenia than acute administration. A number of protocols for chronic PCP animal models have been developed, with different effects. The effects of some, but not all protocols can be reversed by treatment with antipsychotics. In a primate model, PCP was found to induce cognitive impairments which were reversed with clozapine. See, for example, Jones et al. (2011, British J Pharmacol 164:1162-1194).

Serotonin: serotonin is a monamine neurotransmitter, the activity of which has been associated with SCZ. The psychedelic drug classes indoleamines and phenethyl amines can affect serotoninergic 5-HT2A receptors. LSD, an indoleamine, affects startle habituation and prepulse inhibition of startle, which are indicators of human schizophrenia. See, for example, Marcotte et al. (2001, J Psychiatry & Neuroscience 26:395-410).

GABA: γ-Aminobutyric acid (GABA) is a major inhibitory neurotransmitter. The GABAergic system may be involved in schizophrenia due to its interactions with the dopaminergic system. Picrotoxin, an antagonist of the GABA receptor, produces prepulse inhibition of startle in rats. Haloperidol, an antipsychotic drug, reduces this effect. See, for example, Marcotte et al. (2001, J Psychiatry & Neuroscience 26:395-410).

Kits

Diagnostic and therapeutic kits are also encompassed herein. Kits may comprise a container with a label. Suitable containers include, for example, bottles, vials, and test tubes. The containers may be formed from a variety of materials such as glass or plastic.

Such containers may comprise a composition which includes a probe or an array that could be used to determine a CDKN3/KAP, BTK, PTPRG, SLC39A13, and/or TGM5 haplotype, which could be used for diagnostic or pharmacogenomic applications. Accordingly, labels may indicate that a composition is suitable for use in a specific diagnostic or pharmacogenomic application, and may also indicate directions for either in vivo or in vitro use, such as those described above. The kit of the invention will typically comprise the container described above and one or more other containers comprising materials including, for example, buffers, diluents, filters, needles, syringes, and package inserts with instructions for use.

Also encompassed are kits comprising a probe that hybridizes with a region of human chromosome as described herein that can be used to detect a polymorphism related to a CDKN3/KAP, BTK, PTPRG, SLC39A13, or TGM5 haplotype. The kit may include one or more other elements including: instructions for use; and other reagents, e.g., a label, or an agent useful for attaching a label to the probe. A kit may include a label, e.g., any of the labels described herein above. In certain embodiments, a kit may include a labeled probe that hybridizes to a region of human chromosome as described herein, e.g., a CDKN3/KAP, BTK, PTPRG, SLC39A13, or TGM5 SNV as described herein.

Kits described herein may include instructional material that is directed to the intended use or uses of the kit in question. As used herein, an "instructional material" includes a publication, recording, diagram, or any other medium of expression that directs or dictates the use of the components of a kit for performing the function of a method of the invention described herein. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

Unless otherwise indicated, the present invention utilizes standard techniques well known to practitioners of molecular biology and described in several laboratory protocol handbooks, including: *Molecular Cloning: A Laborato Manual*, Sambrook et al. eds., Cold Spring Harbor Laboratory Press (1989); Ausubel et al. eds., *Current Protocols in Molecular Biology*, John Wiley & Sons, NY, N.Y. (1995).

EXAMPLE I

The present study was built upon the Jerusalem Perinatal Study (JPS) cohort, a population-based research resource derived from births in 1964-76. Originally planned for the study of hypertension in pregnancy, it was expanded to capture other obstetric information. The design, methods and characteristics of the population have been described in detail (Davies et al. Isr. J. Med. Sci. 1969; 5:1095-1106; Harlap et al. Isr. J Med. Sci. 1977; 13:1073-1091). Briefly, the JPS recorded all births to Israeli women living in Jerusalem (and its rural area) and actively surveyed infant mortality and birth defects from multiple sources. In the 3 largest obstetric units, data were abstracted from labor-ward log books, describing maternal conditions, obstetric complications and interventions. Antenatal and intra-partum care were free of charge and equally accessible; care during labors and deliveries was normally provided by midwives. Of 92,539 births, 91,252 were live births. The JPSS-1 study was an interdisciplinary collaboration between epidemiologists and psychiatrists in the U.S. and Israel, and government officials in Israel.

As described herein, the present inventors set out to apply genomic strategies (a) to identify de novo expansions of unstable genomic repeats, (b) to identify de novo cytogenetic changes represented by copy number variants, and (c) to carry out an exploratory screen for de novo events that lead to transcriptional silencing among 35-70 sampled cases born to fathers older than 45 years.

Methods and Materials

Blood Samples:

After informed consent was received, the blood samples were drawn by a licensed, registered and insured nurse on the JPS research team. They were placed in 3 vaccutainers: two 5 cc purple top (edta) and one 7 cc red top (serum container). The 2 EDTA vaccutainers were immediately wrapped carefully to prevent breaking and placed in a cooler bag containing an ice pack, while the serum container was placed separately in a closed box to prevent its exposure to light and maintained at room temperature. The exact time was recorded and each test tube was given a sticker with a research identification number specific to the subject. When all the samples were gathered for the day, the nurse transported them to the lab for processing; typically within a few hours and never exceeding 24 hours. Fresh blood was retained; other samples were centrifuged at 4° C. for 20 minutes at 3000 rpm. After, the following steps were taken: 1) plasma (in edta vaccutainer) was separated into 5 cryotubes (0.05 cc a piece); 2) white blood cells (EDTA vaccutainer) were separated into 2 cryotubes; 3) and the serum was kept in the dark in transport and until the separation in the lab for 1 hour. After separation, it was placed in 3 cryotubes. These blood components were then stored in a freezer at −80° C.

To date a total of 51 blood samples have been collected (30 SCZ probands, 7 mothers, 4 fathers, 4 brothers, and 6 sisters). 41 of the samples were delivered to the lab within a couple of hours, while 10 were delivered the next day (within 24 hours). Only in one sample was there a problem processing the blood. In this particular case there was not enough serum to separate into 3 cryotubes, so less was used. All other blood samples were successfully processed.

As indicated herein, the present inventor set out to identify de novo events in JPSS trios. This was accomplished by the following steps: 1) Identify JPSS trios with affected proband and unaffected parents and negative family history of schizophrenia; 2) Exome sequence proband and parents from blood-based DNA (Nimblegen exome v2, 44 MB: all CCDS and RefSeq coding exons and splice regions, 731 miRNAs); and 3) Multiplex 4 libraries per lane on v3 flowcell on our HiSeq: median>100× coverage, 93% of bp≥10× coverage per sample.

Once the sequences were determined, the following steps were performed: 1) Align and identify SNVs and indels with in-house scripts; 2) Filter for variants present in proband but not in either parent, looking in particular for frameshift or nonsense mutations; splice mutations ±3 bp; or missense mutations with a Polyphen-2 score >0.90 or SIFT P<0.05; and 3) further assess/validate based on filtering set of >800 in-house unrelated exomes. Sanger sequencing was performed to validate the sequence information obtained.

Results

As indicated herein above, a remarkable finding of the present study is the linear effect of advancing paternal age effect on the risk for SCZ. Each decade multiplied the risk of SCZ by 1.4 (1.2-1.7, p<0.0001), so the relative risk for offspring of fathers aged 45+ was 3.0 (1.6-5.5) vs. fathers age 20-24, after control of maternal age. The attributable risk (or proportion) for paternal age in this cohort is large, 26%, suggesting that it could play a role in a substantial proportion of cases.

Further to the above, the first 14 trios analyzed have revealed the presence of five validated de novo mutations in five different genes that are associated with SCZ in families with no known history of SCZ. The five different genes are Kinase-associated phosphatase, cell cycle control protein (CDKN3/KAP); Bruton's tyrosine kinase (BTK); Protein tyrosine phosphatase receptor (PTPRG); the Zinc transporter (SLC39A13); and transglutaminase 5 (TGM5). These genes and the point mutation therein and positional location thereof are depicted in FIGS. 1-5.

The designation in FIGS. 1-5 of an EVS of 0 refers to a point mutation that is novel based on Washington University Exome variation scores. See NHLBI Exome Variant Server (EVS): (http://evs.gs.washington.edu/EVS/). This site contains data from 6,500 exomes completed at the University of Washington, which is useful in population-level filtering based on minor allele frequency. The database is searchable via a web tool and downloadable.

A PolyPhen 2 score (PP2) predicts change in function of a mutation in the gene. See dbNSFP (https://sites.google.com/site/jpopgen/dbNSFP—database for Nonsynonymous SNPs' functional predictions; predictions from SIFT, PolyPhen2, LRT, MutationTaster and conservation score (PhyloP) for every potential SNV in the genome. A polyphen of 1.000 indicates the likelihood that the mutation in question is associated with an increase in activity in the protein encoded by the gene comprising the SNV.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of treating a mammalian subject afflicted with schizophrenia comprising, a) identifying a mammalian subject with schizophrenia and having a haplotype comprising a mutated BTK (Bruton's Tyrosine Kinase) gene which comprises a mutation in the codon encoding amino acid 255 of the BTK protein, and b) administering a BTK inhibitor to the subject.

2. The method of claim 1, wherein the mutation replaces arginine at amino acid position 255 with glutamine in the BTK protein.

3. The method of claim 1, wherein the BTK inhibitor is PCI-32765, PCI-33380, PCI-29732, AVL-292, or ONO-WG-307.

4. The method of claim 1, wherein the haplotype further comprises a mutated protein tyrosine phosphatase receptor (PTPRG) gene.

5. A method of diagnosing and treating a mammalian subject with schizophrenia comprising,
   a) obtaining a nucleic acid sample from a mammalian subject,
   b) detecting in said sample, a haplotype comprising a mutated BTK gene which comprises a mutation in the codon encoding amino acid 255 of the BTK protein and optionally, a mutation in the codon encoding amino acid 422 of the PTPRG protein whereby the mutation introduces a stop codon at amino acid position 422,
   c) diagnosing the subject with schizophrenia, and
   d) administering a BTK inhibitor to the subject.

6. The method of claim 5, wherein the mutation in the BTK gene replaces arginine at amino acid position 255 with glutamine in the BTK protein.

7. The method of claim 1, wherein the mammalian subject exhibits symptoms indicative of schizophrenia.

8. The method of claim 5, wherein the mammalian subject exhibits symptoms indicative of schizophrenia.

9. The method of claim 1, wherein the identifying is performed by analyzing a sample isolated from the mammalian subject.

10. The method of claim 9, wherein the sample is blood, plasma, lymph, buccal cells, or a tissue biopsy.

11. The method of claim 7, wherein the sample is blood, plasma, lymph, buccal cells, or a tissue biopsy.

12. The method of claim 1, wherein the identifying is performed by nucleic acid sequencing.

13. The method of claim 5, wherein the detecting step is performed by nucleic acid sequencing.

14. The method of claim 5, wherein the mammalian subject has a haplotype that comprises both of the mutated genes.

15. A method of treating a mammalian subject afflicted with schizophrenia and having a haplotype comprising a mutated BTK gene which comprises a mutation in the codon encoding amino acid 255 of the BTK protein, the method comprising administering a BTK inhibitor to the subject.

16. The method of claim 15, wherein the mutation in the BTK gene replaces arginine at amino acid position 255 with glutamine in the BTK protein.

17. The method of claim 15, wherein the mammalian subject exhibits symptoms indicative of schizophrenia.

18. The method of claim 15, wherein the haplotype further comprises a mutated protein tyrosine phosphatase receptor (PTPRG) gene.

19. The method of claim 15, wherein the BTK inhibitor is PCI-32765, PCI-33380, PCI-29732, AVL-292, or ONO-WG-307.

20. The method of claim 5, wherein the BTK inhibitor is PCI-32765, PCI-33380, PCI-29732, AVL-292, or ONO-WG-307.

21. A method of treating a mammalian subject suspected of having schizophrenia comprising:
   a) identifying a mammalian subject having a haplotype encoding a mutated BTK gene which comprises a mutation in the codon encoding amino acid 255 of the BTK protein and exhibiting symptoms indicative of schizophrenia, and b) administering a BTK inhibitor to said subject.

22. The method of claim 21, wherein the mutation in the BTK gene replaces arginine at amino acid position 255 with glutamine in the BTK protein.

23. The method of claim 21, wherein the BTK inhibitor is PCI-32765, PCI-33380, PCI-29732, AVL-292, or ONO-WG-307.

24. The method of claim 21, wherein the haplotype further comprises a mutated protein tyrosine phosphatase receptor (PTPRG) gene.

25. The method according to claims 7, 8, 17, or 21, wherein the symptoms indicative of schizophrenia comprise at least one of hallucinations, delusions, social deficits, disorganized language and behavior, and mild cognitive dysfunction.

26. The method according to claim 1, 5, 15, or 21, wherein the mammalian subject is free of detectable cancer.

\* \* \* \* \*

UNITED STATES PATENT AND TRADEMARK OFFICE
CERTIFICATE OF CORRECTION

PATENT NO. : 9,714,450 B2
APPLICATION NO. : 14/016597
DATED : July 25, 2017
INVENTOR(S) : Dolores Malaspina Page 1 of 1

It is certified that error appears in the above-identified patent and that said Letters Patent is hereby corrected as shown below:

In the Specification

At Column 1, Lines 14-17, replace:
"The research leading to the present invention was funded in part by grant number R01MH059114 from the National Institute of Health. The United States government has certain rights in the invention."

With:
--This invention was made with government support under grant number R01 MH059114 awarded by the National Institutes of Health. The government has certain rights in the invention.--

Signed and Sealed this
Twenty-first Day of May, 2019

Andrei Iancu
*Director of the United States Patent and Trademark Office*